United States Patent
Van Pelt

(10) Patent No.: US 10,077,859 B2
(45) Date of Patent: Sep. 18, 2018

(54) COMPRESSION CONNECTION

(71) Applicant: Colleen K. Van Pelt, Groton, NY (US)

(72) Inventor: Colleen K. Van Pelt, Groton, NY (US)

(73) Assignee: CORSOLUTIONS LLC, Groton, NY (US)

( * ) Notice: Subject to any disclaimer, the term of this patent is extended or adjusted under 35 U.S.C. 154(b) by 1034 days.

(21) Appl. No.: 14/483,997

(22) Filed: Sep. 11, 2014

(65) Prior Publication Data
US 2014/0375048 A1 Dec. 25, 2014

Related U.S. Application Data

(60) Division of application No. 12/625,067, filed on Nov. 24, 2009, now Pat. No. 8,851,528, which is a
(Continued)

(51) Int. Cl.
| | |
|---|---|
| *F16L 19/065* | (2006.01) |
| *B01L 3/00* | (2006.01) |
| *G01N 30/72* | (2006.01) |

(52) U.S. Cl.
CPC ............ *F16L 19/065* (2013.01); *B01L 3/565* (2013.01); *G01N 30/7266* (2013.01);
(Continued)

(58) Field of Classification Search
CPC ........ G01N 30/16; G01N 30/62; G01N 30/64; G01N 30/66; G01N 30/68; G01N 30/70; G01N 30/72; G01N 30/7213; G01N 30/722; G01N 30/7233; G01N 30/724; G01N 30/7246; G01N 30/7253; G01N 30/726;
(Continued)

(56) References Cited

U.S. PATENT DOCUMENTS

| 3,498,027 A | 3/1970 | Buchtel, Jr. |
| 3,589,170 A | 6/1971 | Praglin et al. |

(Continued)

FOREIGN PATENT DOCUMENTS

| WO | 20050119110 A2 | 12/2005 | |
| WO | 20060083597 A2 | 8/2006 | |
| WO | WO-2012058513 A1 * | 5/2012 | ........... G01N 30/461 |

OTHER PUBLICATIONS

International Search Report for International Patent Application No. PCT/US07/75817 (dated Aug. 25, 2008).
(Continued)

*Primary Examiner* — James M Hewitt, II
(74) *Attorney, Agent, or Firm* — Bond, Schoeneck & King, PLLC; Joseph Noto

(57) ABSTRACT

A system for the automated compression connection of fluidic components includes receiving hardware configured to align an insert placed therein: an interchangeable plug-and-play consumable insert configured for automated connection to the receiving hardware: a drive force mechanism: and at least one mechanical support wherein the drive force mechanism is configured to apply a substantially axial drive force opposed by the at least one mechanical support to align and compress the insert to create a leak-resistant seal between the insert and the receiving hardware, such that the system provides automated alignment and sealing of the insert.

3 Claims, 36 Drawing Sheets

Related U.S. Application Data continuation of application No. 11/837,989, filed on Aug. 13, 2007, now Pat. No. 7,641,242.

(60) Provisional application No. 60/822,231, filed on Aug. 12, 2006.

(52) U.S. Cl.
CPC ...... *B01L 2300/0838* (2013.01); *Y10S 285/92* (2013.01); *Y10T 137/6851* (2015.04)

(58) Field of Classification Search
CPC ........... G01N 30/7266; G01N 30/7273; G01N 30/728; G01N 30/7286; G01N 30/7293; G01N 2030/642; G01N 2030/645; G01N 2030/647; G01N 2030/685; G01N 2030/7226; G01N 2030/6013; B01D 15/08; B01D 15/10; B01D 15/22
USPC ............. 210/198.2, 656; 285/31, 332, 332.1, 285/332.2, 332.3, 342, 920; 96/106; 73/40, 46

See application file for complete search history.

(56) References Cited

U.S. PATENT DOCUMENTS

| | | | |
|---|---|---|---|
| 4,083,702 A | 4/1978 | Hartigan et al. | |
| 4,524,616 A | 6/1985 | Drexel et al. | |
| RE31,974 E | 8/1985 | Brownlee | |
| 4,549,965 A | 10/1985 | Davis | |
| 4,913,464 A | 4/1990 | Taylor et al. | |
| 4,991,883 A | 2/1991 | Worden | |
| 5,080,785 A | 1/1992 | Allington et al. | |
| 5,090,871 A | 2/1992 | Story et al. | |
| 5,169,120 A | 12/1992 | Guthrie, Jr. et al. | |
| 5,221,521 A | 6/1993 | Hashizume et al. | |
| 5,222,769 A | 6/1993 | Kaempen | |
| 5,228,338 A | 7/1993 | Saghatchi | |
| 5,275,445 A | 1/1994 | Krings et al. | |
| 5,288,113 A | 2/1994 | Silvis et al. | |
| 5,343,736 A | 9/1994 | Cady et al. | |
| 5,379,790 A | 1/1995 | Bruce et al. | |
| 5,482,628 A | 1/1996 | Schick | |
| 5,540,464 A | 7/1996 | Picha | |
| 5,580,103 A | 12/1996 | Hall | |
| 5,601,785 A | 2/1997 | Higdon | |
| 5,645,301 A | 7/1997 | Kingsford et al. | |
| 5,772,643 A | 6/1998 | Howell et al. | |
| 5,819,708 A | 10/1998 | Buratti et al. | |
| 5,911,954 A | 6/1999 | Ford et al. | |
| 6,223,584 B1 | 5/2001 | Mustacich et al. | |
| 6,267,143 B1 | 7/2001 | Schick | |
| 6,428,053 B1 | 8/2002 | Tai et al. | |
| 6,709,027 B2 | 3/2004 | Rittenhouse | |
| 7,010,964 B2 | 3/2006 | Karp et al. | |
| 7,014,222 B1 | 3/2006 | Poppe | |
| 7,077,436 B1 | 7/2006 | Krywitsky | |
| 7,338,088 B2 | 3/2008 | Salven et al. | |
| 7,475,916 B2 | 1/2009 | Muller et al. | |
| 7,641,242 B2 | 1/2010 | Van Pelt | |
| 7,681,926 B2 | 3/2010 | Valaskovic et al. | |
| 2002/0093143 A1 | 7/2002 | Tai et al. | |
| 2004/0245779 A1 | 12/2004 | Russell | |
| 2007/0000828 A1 | 1/2007 | Norman et al. | |
| 2007/0084982 A1* | 4/2007 | Martone | G01N 30/6047 248/316.8 |
| 2010/0154207 A1* | 6/2010 | Ford | G01N 30/6004 29/700 |
| 2012/0305092 A1* | 12/2012 | Corso | B01L 3/502715 137/15.01 |

OTHER PUBLICATIONS

Peng et al., "Evaluation of Multidimensional Chromatography Coupled with Tandem Mass Spectrometry (LC/LC-MS/MS) for Large-Scale Protein Analysis: The Yeast Proteome," Journal of Proteome Research 2:43-50 (2003).

Shen et al., "Packed Capillary Reversed-Phase Liquid Chromatography with High-Performance Electrospray Ionization Fourier Transform Ion Cyclotron Resonance Mass Spectrometry for Proteomics," Analytical Chemistry 73 (8): 1766-75 (2001).

Supplemental European Search Report for European Patent Application No. EP07871021 (dated Jul. 12, 2010).

Washburn et al., "Large-Scale Analysis of the Yeast Proteome by Multidimensional Protein Identification Technology," Nature Biotechnology 19:242-7 (2001).

Wilm et al., "Analytical Properties of the Nanoelectrospray Ion Source," Analytical Chemistry 68(1):1-8 (1996).

Written Opinion of the International Searching Authority for International Patent Application No. PCT/US07/75817 (dated Aug. 8, 2008).

* cited by examiner

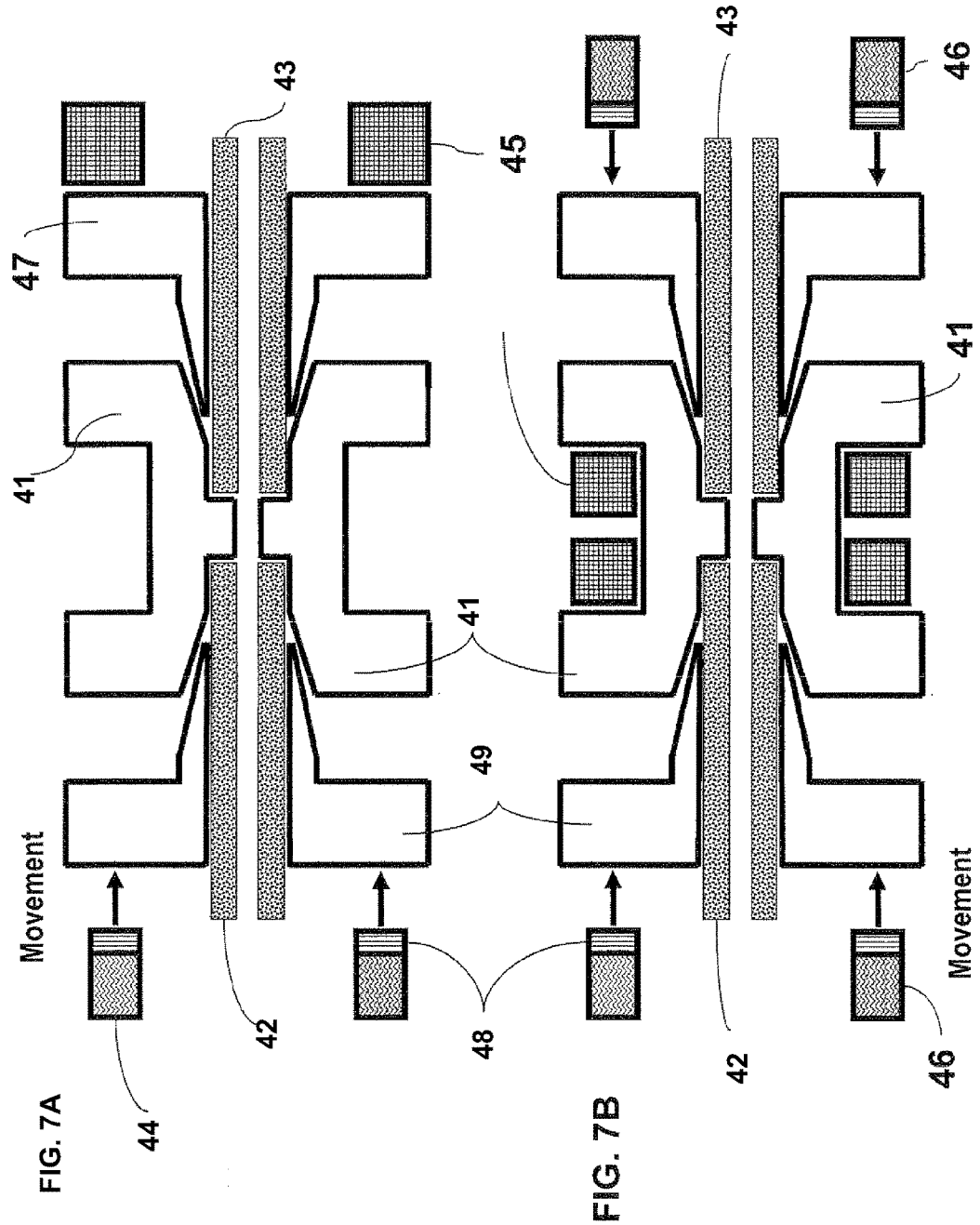

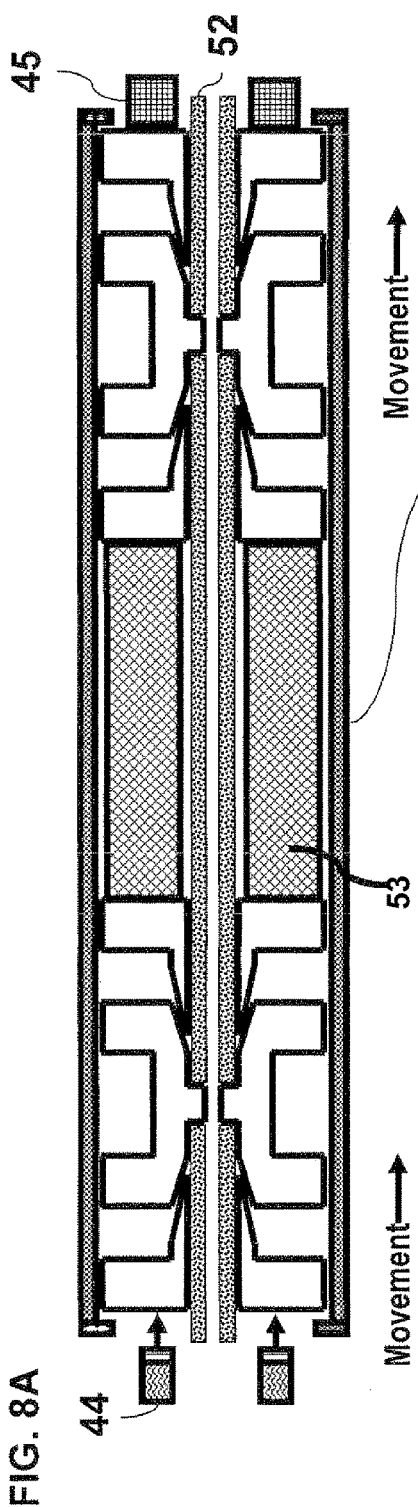
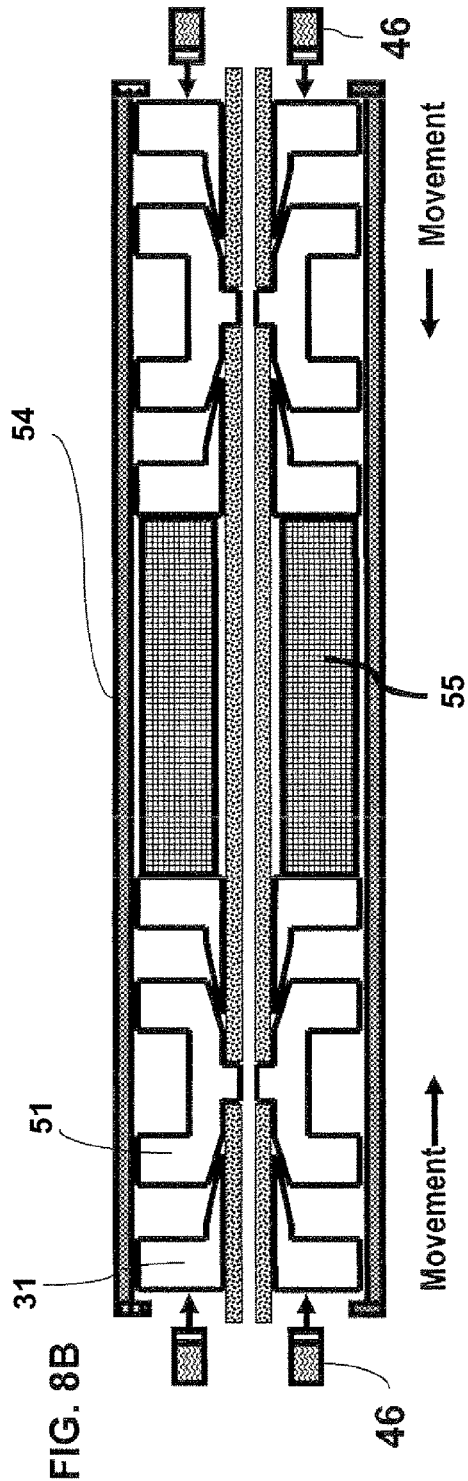
FIG. 8A    FIG. 8B    FIG. 8

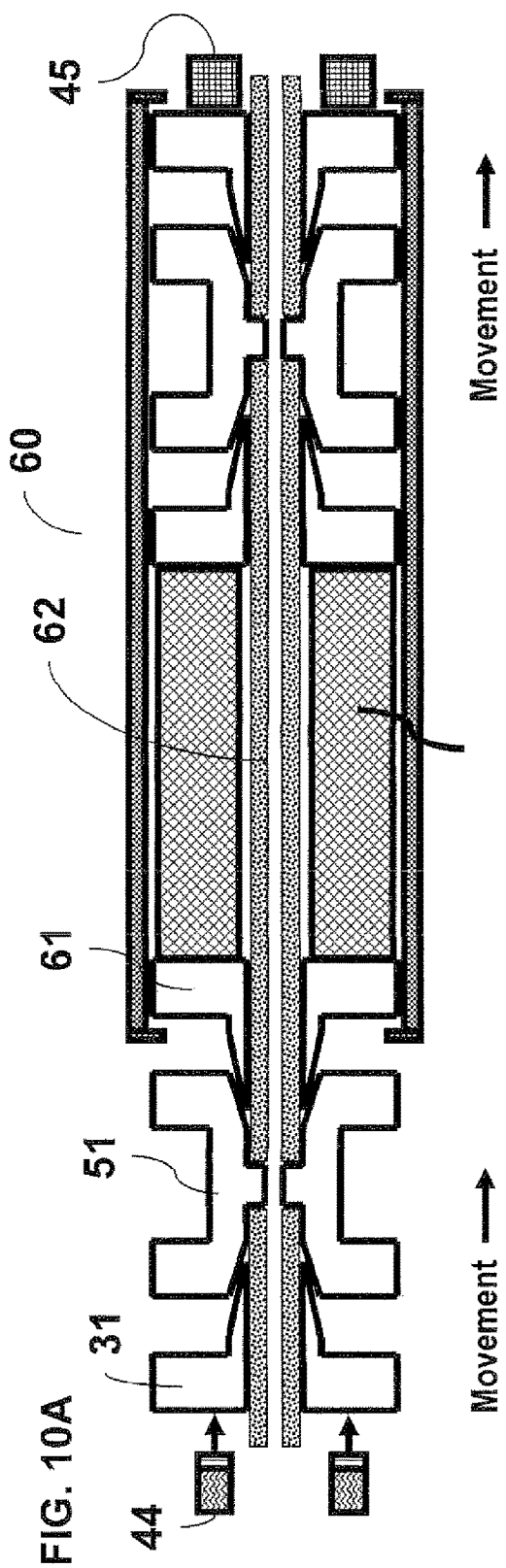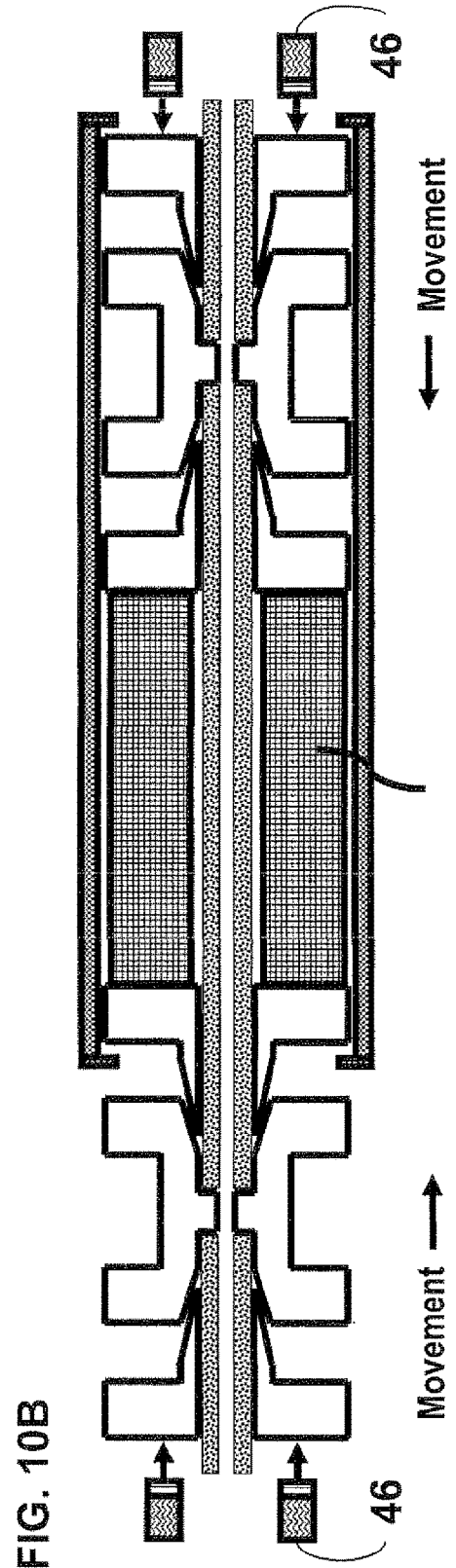

COMPRESSION CONNECTION

CROSS-REFERENCE TO RELATED APPLICATIONS

This application is a divisional of U.S. patent application Ser. No. 12/625,067 filed Nov. 24, 2009, now U.S. Pat. No. 8,851,528, which is a continuation of application Ser. No. 11/837,989, filed Aug. 13, 2007, now U.S. Pat. No. 7,641,242, which claims the benefit of U.S. Provisional Application Ser. No. 60/822,231, filed Aug. 12, 2006, and their entire contents are hereby incorporated by reference.

FIELD OF THE INVENTION

The present invention relates generally to a chromatography and fluidics system, and more specifically to a chromatography electrospray system with "plug and play" connections along with integrated leak and current sensors for monitoring and diagnosing the status of ultra-low level fluidic manipulation. In particular, the present invention relates to an integrated nanofluidic separation system and electrospray device. This achieves a significant advantage over other conventional low-flow chromatography electrospray systems that lack the means and technology to diagnose individual component performance and operation. This present invention allows for component diagnostics in chromatography and fluidic systems. The present invention further provides the ability to implement an automated replacement system capable of making fluidic connections. Furthermore, the connections of the invention are automatically sealed with the proper force, eliminating the need for the user to guess the correct amount of compression force to apply when tightening fittings.

BACKGROUND OF THE INVENTION

Nanoflow liquid chromatography ("nanoLC") is a technique for resolving very complex samples that are limited in concentration or volume. Predominantly the technique is used for proteomic studies where it is often used in combination with mass spectrometry. NanoLC of either whole proteins or a proteolytic digest is performed to separate very complex samples, and then the flow from the nanoLC is directed into a mass spectrometer. The advantages of nanoLC mass spectrometry as compared to conventional higher flow rate chromatography include lower sample volume requirements and higher sensitivity. NanoLC separation reduces the complexity of the sample by resolving the different components of a sample, allowing the mass spectrometer to obtain mass spectra for many components contained in the sample.

A liquid chromatography/mass spectrometry (LC/MS) system is composed of a pumping system, an autosampler injection system, a chromatography column(s), a means of ionization, and a mass spectrometer detector. The pumping system delivers mobile phase (solvents) at a user defined flow rate, typically ranging from 20 nL/min to 6 mL/min. Mobile phases generally consist of two solvents where one is predominantly aqueous (water) in nature and the other is predominantly organic in nature (methanol, acetonitrile, isopropanol, etc). Additives such as formic acid, acetic acid, ammonium acetate, ammonium hydroxide, etc, can also be present in the mobile phase. The pumping system delivers the different solvents of the mobile phase in a precise way that is referred to as the gradient. For an analysis using a reversed-phase column, the gradient typically begins with high aqueous solvent and gradually organic solvent is introduced, while the overall flow rate remains constant. By the end of the analysis, the mobile phase content is predominantly organic solvent.

The target sample of interest is introduced to the flow stream by the autosampler injection system. This system typically consists of an aspiration needle and a valve. The system aspirates the sample of interest using the needle and subsequently injects the sample into the injection valve. This valve has a sample loop that can be 1 microliter to 10 milliliters in volume, and is filled with the sample of interest. Then the valve is switched from the "load" position to the "inject" position, and the plug of sample from the loop becomes in-line with the flowing mobile phase from the pumping system. The mobile phase displaces the sample plug from the loop and pushes it into the analysis path. At this point the pumps would be early in the gradient program, so that the sample plug is in predominantly aqueous solvent.

The sample continues flowing downstream and reaches the column. As the mobile phase is predominantly aqueous in nature, the sample adsorbs to the stationary phase at the top of the reversed-phase column. As the analysis is performed the solvent composition of the mobile phase becomes increasingly organic in content. As this occurs, mass transfer of the retained molecules occurs between the stationary and mobile phases. The components of the sample make their way through the column at different rates, and thus the sample is chromatographically resolved.

The various components of the sample exit the column at different time points in the flowing mobile phase. As the mass spectrometer is only able to detect ions, not neutral molecules, the sample components must be converted to ions prior to entering the mass spectrometer. One means of generating ions is electrospray ionization, which at lower flow rates is referred to as nanoelectrospray ionization. In brief, a high voltage is applied to the column effluent containing the sample components of interest. The high voltage generates highly charged droplets and through subsequent droplet evaporation and droplet fission, desolvated ions are formed.

The ions then enter the mass spectrometer detector. The mass spectrometer determines the mass-to-charge ratio of the ions. Many of these instruments perform tandem mass spectrometric measurements, allowing structural information of the ion to be determined.

At the end of the analysis, the column is washed with high organic solvent and is then re-equilibrated in the aqueous mobile phase. An autosampler routine is used to wash the injection needle and sample loop several times to help minimize sample-to-sample cross-contamination and carryover. At this point a second analysis can be performed.

NanoLC is typically performed at flow rates between 5-500 nL/min. These low flow rates necessitate the use of special pumping systems, chromatography columns, and spray emitters used for the electrospray ionization ("ESI") interface to the mass spectrometer. Even with the specialty equipment currently available nanoLC is very difficult to perform. Making connections with micron size tubing requires user intervention to tighten fittings. As there is no feedback in the system, the user must guess the correct amount of tightening to make the fitting leak-free. Generally, this leads to over tightening of the fittings which may prevent leaking, however, simultaneously creates a secondary problem. The over tightening can either damage the tube, the fitting, or the fragile capillaries. Connecting nanoLC columns is especially difficult as the fragile columns are prone to damage due to frits, stationary phase within the column, or other material in the tube being crushed, cracked, or over compressed. Additionally, the rotation of the conventional fitting can cause the tube or capillary to be twisted, resulting in grinding or damage from the twisting itself.

Connections between the pumping system and column, and between the column and spray emitter are especially prone to leaks. Often the leaks are very difficult to detect as evaporation renders the leak unperceivable at the low flow rate or the liquid build up is so small it is difficult to observe. This holds true for both chip-based microfluidics and conventionally assembled components. Leaks at these connections can be due to user error in making connections, or due to a change in the system backpressure which can result from a clogged column or spray emitter. Further challenges of nanoLC include column irreproducibility, spray irreproducibility, poorly optimized solvent gradient separation, insufficient column regeneration period, and poorly optimized emitter position. Conventional fittings are thread-based requiring rotation of the ferrule, and subsequently the tubing, to generate a seal. The applied twisting motion causes tubing ends to grind against surfaces creating jagged ends and producing particulates that subsequently clog and contaminate fragile components downstream. The challenges associated with nanoLC results in the technique only being successfully used by very few expert users.

Although various research and apparatuses have attempted to reduce the difficulty of conducting nanoLC there is still a need for a simple, robust system with easy to change components and integrated diagnostic sensors for identifying malfunctions in the dynamic fluidic system. This includes conventional, microfluidic, and nanofluidic-based fluidic systems.

Additionally, current technologies provide limited measurements at the pumping level, which is not indicative of component status at the chromatography and electrospray level. Therefore, the current technology lacks the ability to indicate the malfunction location. In addition to not being able to diagnose the problem, these current technologies lack the ability to automatically change-out the appropriate components due to both lack of information and due to instrument design involving connecting fittings that require human intervention.

Therefore there exists a need for an automatic sealing device for making connections in fluidic systems to reduce potential user over tightening and to self-align the components within the fluidic system.

There also exists a need for a prefabricated insert containing multiple fluidic components to reduce the number of connects that a user is required to make.

There exists a need for detecting leaks in microfluidic and nanofluidic applications where sample size and flow rates are too small to be detected by conventional means.

There further exists a need for fluidic system components that are easy to replace and can be interchanged by an automated process.

SUMMARY OF THE INVENTION

The present invention reduces the complexity of fluidic systems. Specifically, of nanoLC by allowing a large number of users to successfully perform the technique. The invention encompasses a simple, "pop-into-place" device which has the nanoLC column and spray emitter incorporated within a single structure. Furthermore, all connections are either pre-made or made when the user inserts the device into its holder in front of the mass spectrometer. The connections are automatically sealed with the proper compression force, eliminating the possibility for the user to over or under tighten the connections. Built-in sensors detect any leaks in the nanoLC system, and a spray sensor monitors the electrospray process. The present invention allows for nanoLC applications beyond proteomics to other areas such as pharmaceutical analyses, forensic analyses, biomarker analyses, environmental analyses, clinical diagnostics, flow-through reactors and other areas requiring more sensitivity and efficiency with a robust and easy-to-use technology.

The present invention contains receiving hardware that can accept one or more "plug and play" components. A positioning sensor assures proper insertion and alignment of the "plug and play" components. In one embodiment the receiving hardware has auto-insertion hardware for proper placement of the packages in the system. The receiving hardware aligns the consumable in front of the detector for optimal detector performance. The hardware and consumable insert can be keyed for accurate alignment and precise placement. This can be accomplished through use of alignment features and mechanical positioning features.

A simple consumable insert or "plug and play" component is inserted into the receiving hardware. The insert contains a nanoLC column and electrospray emitter with integrated sensors for diagnosing system and component failure for fluidic technologies where visual assessment is not possible. The system allows for manual or automated microfluidic connections without the need for user expertise in making difficult and critical fluidic connections. In addition to a column and spray emitter, the insert could also contain a pre-column, a transfer line, a trap, a filter, a frit, a reactor, a union, a tee, a manifold, a mixer, a vessel, a injector, an adapter, a sensor, a backpressure regulator, a coupler, a plug, a loop, a needle, a injector valve, a check valve, a metering valve, a splitting valve, a purge valve, a switching valve, and a Y-connecter.

The present invention contains sensors that operate independent of each other, and a software program logs critical information and monitors component and system operation. The information may then be used to continue system operation, necessitate component or system shutdown, adjust system parameters, or initiate the replacement of necessary components.

The present invention is further capable of diagnosing very small fluidic leaks and nanoflow electrospray failures at the component and system level for conventional, microfluidic, and nanofluidic devices. According to one aspect of the present invention, the leak sensors are integrated into the insert and the corresponding interconnects are made automatically upon placement of the consumable in the accepting hardware.

Integrating all the above features allows for a more robust and "smart" system not available with current chromatography technology. Additionally because the device integrates diagnostic features, not available with current technologies, the system can automatically identify problematic components within a system. This contrasts today's systems that require high user skill to trouble shoot and where repairing the system often involves blind substitution of parts to diagnose the problematic components. The insert can include one or more of the chromatography devices within each insert. Thus one insert for acceptance into the receiving hardware may include one or more liquid chromatography or liquid chromatography electrospray devices. The automated sealing allows for component changing for fluidic applications in general.

The plug-and-play compression connections of the present invention can further be utilized to interface a vessel pre-filled with a target sample of interest to an analysis system. Delivery of the fluid sample to the analysis system may be via displacement using positive or negative pressure.

BRIEF DESCRIPTION OF THE SEVERAL VIEWS OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 7A is a cross-sectional view of a dual-sided receiving port where two separate tubes are sealed via axial force generated by the controlled force compression system. Both tubes are sealed with equal force as there is only a single compression system.

FIG. 7B is a cross-sectional view of a dual-sided receiving port where two separate tubes are sealed via axial force generated by the controlled force compression system. The tubes have independent sealing forces as there are two independent compression mechanisms and the receiving port is braced.

FIG. 8A is a cross-sectional view of an assembly of ferrules and receiving ports where two separate tubes are connected to a column at its inlet and outlet, the controlled force compression system compresses all of the ferrules and receiving ports providing sealed connections.

FIG. 8B is a cross-sectional view of an assembly of ferrules and receiving ports where two separate tubes are connected to a column at its inlet and outlet, separate controlled force compression systems independently compress all of the ferrules and receiving ports on the inlet and outlet sides allowing for independent sealing control and compression strength on both the inlet and outlet sides.

FIG. 10A is a cross-sectional view of an assembly of ferrules and receiving ports where part of the assembly is contained within the insert, the controlled force compression system compresses all of the ferrules and receiving ports thus providing sealed connections.

FIG. 10B is a cross-sectional view of an assembly of ferrules and receiving ports where part of the assembly is contained within the insert, separate controlled force compression systems independently compress the ferrules and receiving ports on the inlet and outlet sides of the column, allowing for independent sealing control and compression strength.

DETAILED DESCRIPTION OF THE INVENTION

Figure 1:
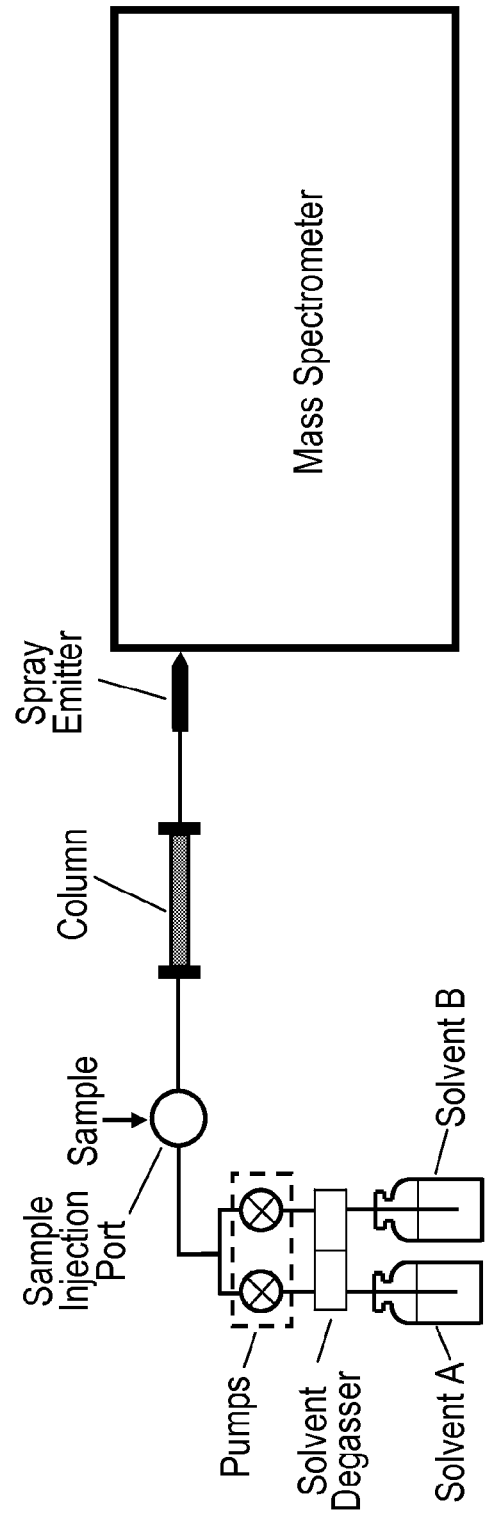
FIG. 1 is a schematic view of a liquid chromatography/mass spectroscopy system according to the prior art.

An aspect of the present invention provides a "pop-in", "plug-and-play", "snap-in", "click-in" or "quick connect" liquid chromatography electrospray device that requires little user expertise. In one embodiment the "plug-and-play" device has integrated performance sensors and detectors. The sensors allow for monitoring of performance at the component and system levels, and provide the option of automated repair or consumable replacement. The "plug-and-play" connections allow for components to be changed in an automated fashion or with limited user skill or know-how. The compression mechanism has a force measuring mechanism that controls the precise amount of force generated. Additionally, the system can monitor the sealing force and make adjustments if necessary due to leaks, change in pressure requirements or for material fatigue. It is understood that the terms "Plug-and-Play", "Quick Connect", "Snap-in", "Click-in", "Pop-in", reference the ability to place the part or component into the corresponding receiving hardware where the part is then integrated into the system in an automated fashion or with limited user intervention and may be used interchangeably. The present invention does not require special tools or user know-how to make high pressure connections such as hand manipulation of fittings, ferrules, or thumb screw nuts. The present invention eliminates the need for a user to determine the correct sealing force needed to make fragile micro and nanofluidic connections leak tight. In one embodiment the compression system or mechanism has a controlling force system capable of applying a pre-determined amount of force. Alternatively, the compression system is capable of maintaining a given amount of force. The system may also include a force limiting system to avoid over compression.

The "plug and play" insert may be a molded or machined package or may be casted in place. The insert may contain one or more separation device, one or more electrospray device, leak sensors, or any combination thereof. The insert may contain a retractable feature for protecting exposed components including a column end or spray emitter.

The "plug and play" connection allows for the connections of one or more liquid or gas streams in tubing or capillaries. The connections may have integrated functionality within the fitting such as particle filters, frits, guard columns, trap columns, reactors, injectors, or particle, monolithic, or affinity stationary phases, or those alike. Alternatively the inserts may have integrated functionality such as particle filters, frits, guard columns, trap columns, reactors, injectors, or particle, monolithic, or affinity stationary phases, or those alike. They may also include or interface with components such as a transfer line, a electrospray emitter, a union, a tee, a manifold, a mixer, a vessel, an adapter, a backpressure regulator, a coupler, a plug, a loop, a needle, a sensor, a injector valve, a check valve, a metering valve, a splitting valve, a purge valve, a switching valve, and a Y-connecter. The connection can connect glass, metal, polymer or polymer-based, composites, or ceramic tubing. Alternatively, structures other than tubes and capillaries could be molded and used with the connections. In one embodiment, a fitting is attached to a column inlet to join the column and a supply stream tube or capillary. The fittings can be part of a system or they may be independent of hardware if used to connect unrestricted tubing, capillaries or substrates. If the connection is integrated into a hardware platform, the component with the connection can be replaced via robotics or other hardware manipulators and the compression device can automatically compress the fittings. The fittings may be casted, molded, machined, monolithic in nature, or compiled from multiple components. The fitting may hold up to 100,000 PSI, however this force can increase as technology advances. The fitting receives a constant pressure in the axial direction. The constant compression connection of the instant invention is less prone to leaks as compared to the conventional thread-type chromatography connections as conventional fittings often fatigue, slip, or loosen over time and require additional force to be reapplied by further tightening of the fittings. The fittings may be used to connect preparative, analytical, micro, nano, and pico chromatography columns, as well as CE, CEC, capillary tubes, flow-through reactors, sample injectors, and chip-based separation structures and features, such as channels that are packed or unpacked.

In one embodiment the liquid chromatography electrospray system has disposable components that are affixed to the main instrument housing or receiving hardware that is interfaced to an electrospray device. Independent sensors monitor and control the various components in the liquid chromatography electrospray device. The sensors allow for the detection of various diagnostic and performance measurements such as leaks, spray current, system pressure, reaction kinetics, and flow rate in given regions of the device. The invention contains sensors that allow for diagnostic measurements and automated repair of malfunctioning components. This automation also allows for columns of various stationary phase chemistries to be implemented without user intervention. Additionally, the electronic data system can indicate the status of the system by recording the sensor information or system parameters to a remote site or user via wired or wireless communication technologies. The electronic data system may also receive information and conduct future actions based on the received information or commands. In addition to allowing automatic change-out of inserts and components, the present invention's fitting connection design allows for low skilled users to make leak-tight connections.

Shown in FIG. 1 is a schematic view of a liquid chromatography/moss spectroscopy system according to the prior art. The liquid delivery pump delivers solvent A and solvent B to the column. In the sample injection part the sample is injected into the flow of the solvents at a predetermined time by an injector valve. The sample is then delivered to and through the column to the spray nozzle. The spray nozzle delivers the sample to the mass spectrometer where the sample is the analyzed. The data is then sent to the data processing part and information is generated at the display part. The control part allows for the system to be automated and can adjust the timing of particular operations as needed. Additionally, an autosampler may be used to inject the sample in the sample injection part.

Figure 2:
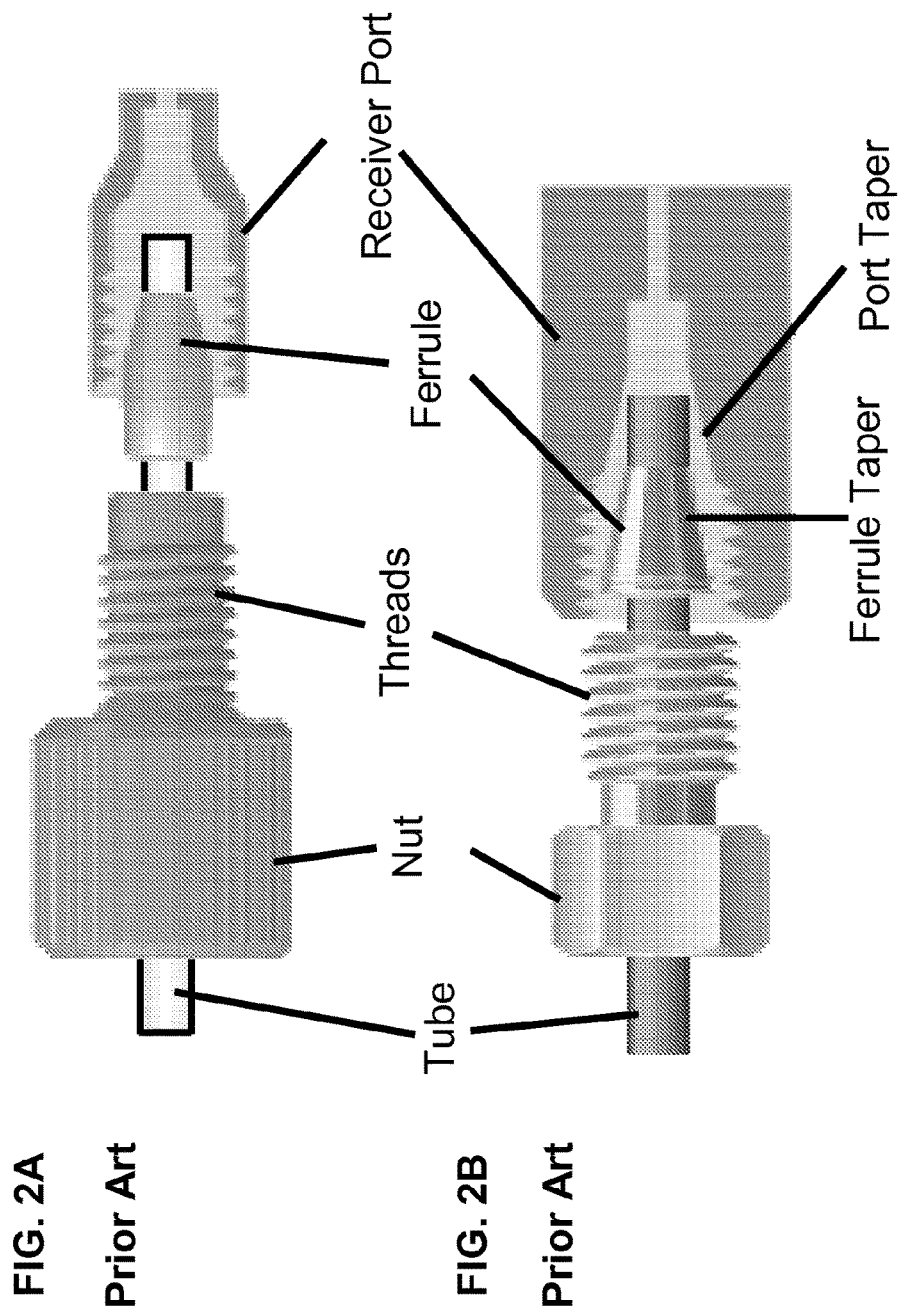
FIG. 2A is a representation of a compression fitting according to the prior art.
FIG. 2B is a representation of a compression fitting according to the prior art.

FIGS. 2A and 2B are representation of a compression fitting according to the prior art. Traditional fittings utilize frusto-conical compression to hold tubing lengths together. Typically a singular plane of contact is made around the circumference of the tube when the 30 degree tapered ferrule tip is compressed against the 45 degree interior taper of the receiver port body. As the nut is tightened into the receiver port body, the compression is intensified. Though effective, attention to technique is required to make a clean, secure connection without inadvertently creating deformations or fractures in the tubing. These fractures would subsequently generate shards of fused silica that could find their way downstream, creating clogs and other system issues. In addition to conical force, twisting motion pushes the tubing ends toward each other. Because no radial slippage occurs, tubing ends are ground together; upon grinding, imperfections or jagged ends in cleaved tubing can produce thousands of fused-silica particulates. The end result is tip clogging and failure.

Figure 3:
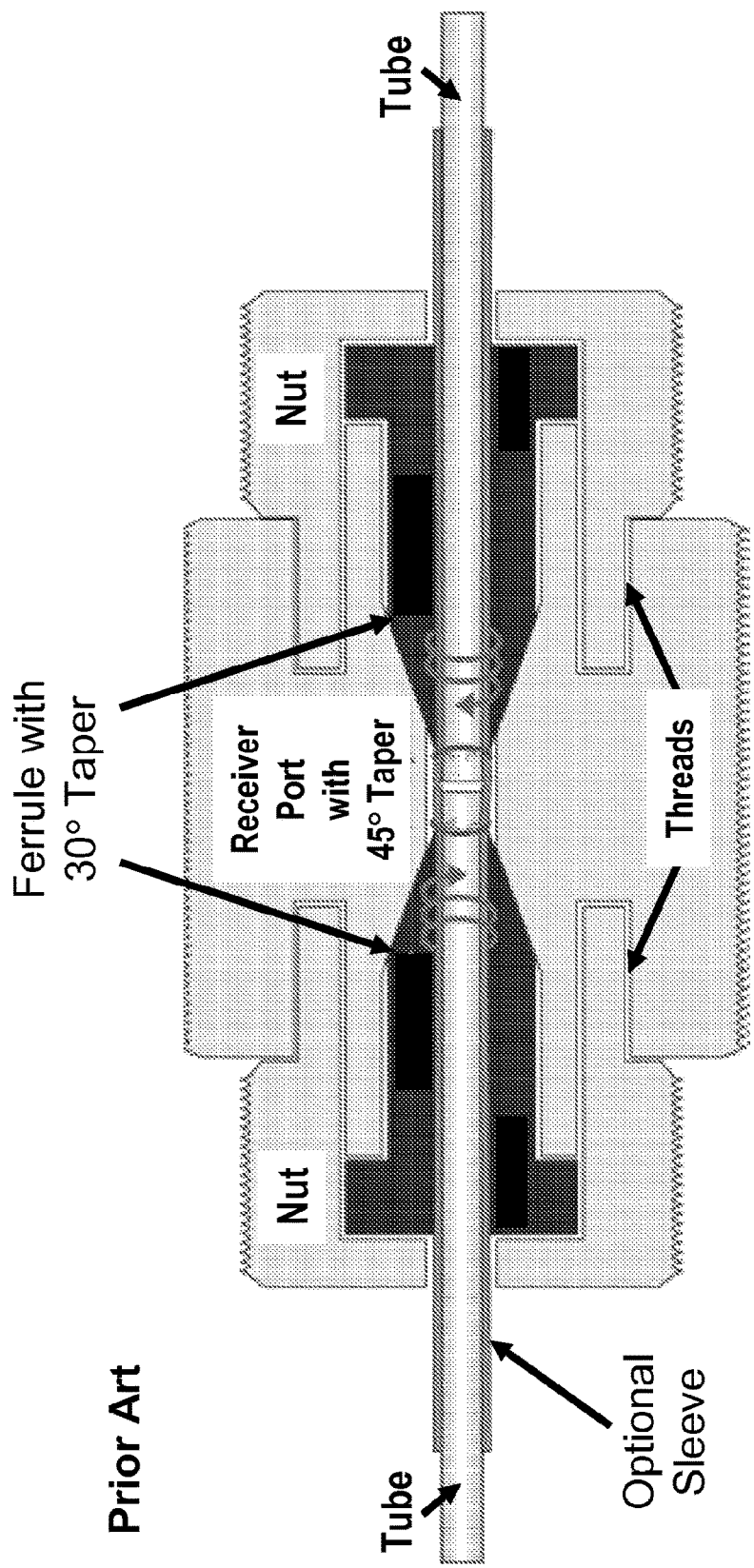
FIG. 3 is a representation of a compression fitting and sleeve according to the prior art.

FIG. 3 is a representation of a compression fitting and sleeve according to the prior art. A connection is made similar to the compression fitting in FIG. 2 with the addition of a sleeve. The sleeve surrounds the circumference of the tube allowing for the use of a ferrule with a larger bore throughout its axial length.

Various modifications to the preferred embodiment will be readily apparent to those skilled in the art, and the general principles defined herein may be applied to other embodiments and applications without departing from the spirit and scope of the invention. Thus, the present invention is not intended to be limited to the embodiments shown, but is to be accorded to the widest scope consistent with the principles and features disclosed herein.

Figure 4:
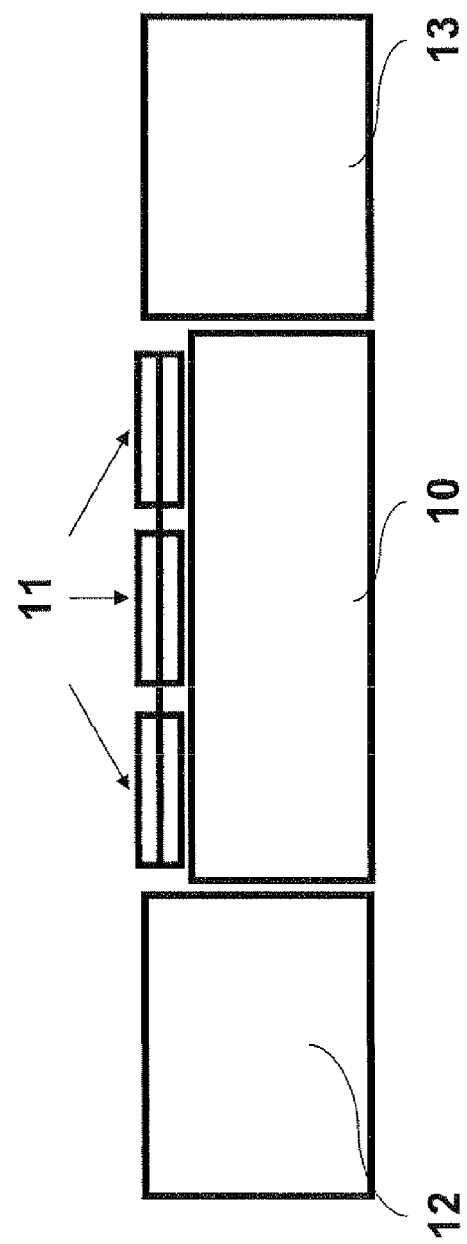
FIG. 4 is a block diagram of the "plug-and-play" insert devices, the receiving compression hardware, a fluid delivery system and fluid processing hardware.
Figures 32, 32A, 32B:
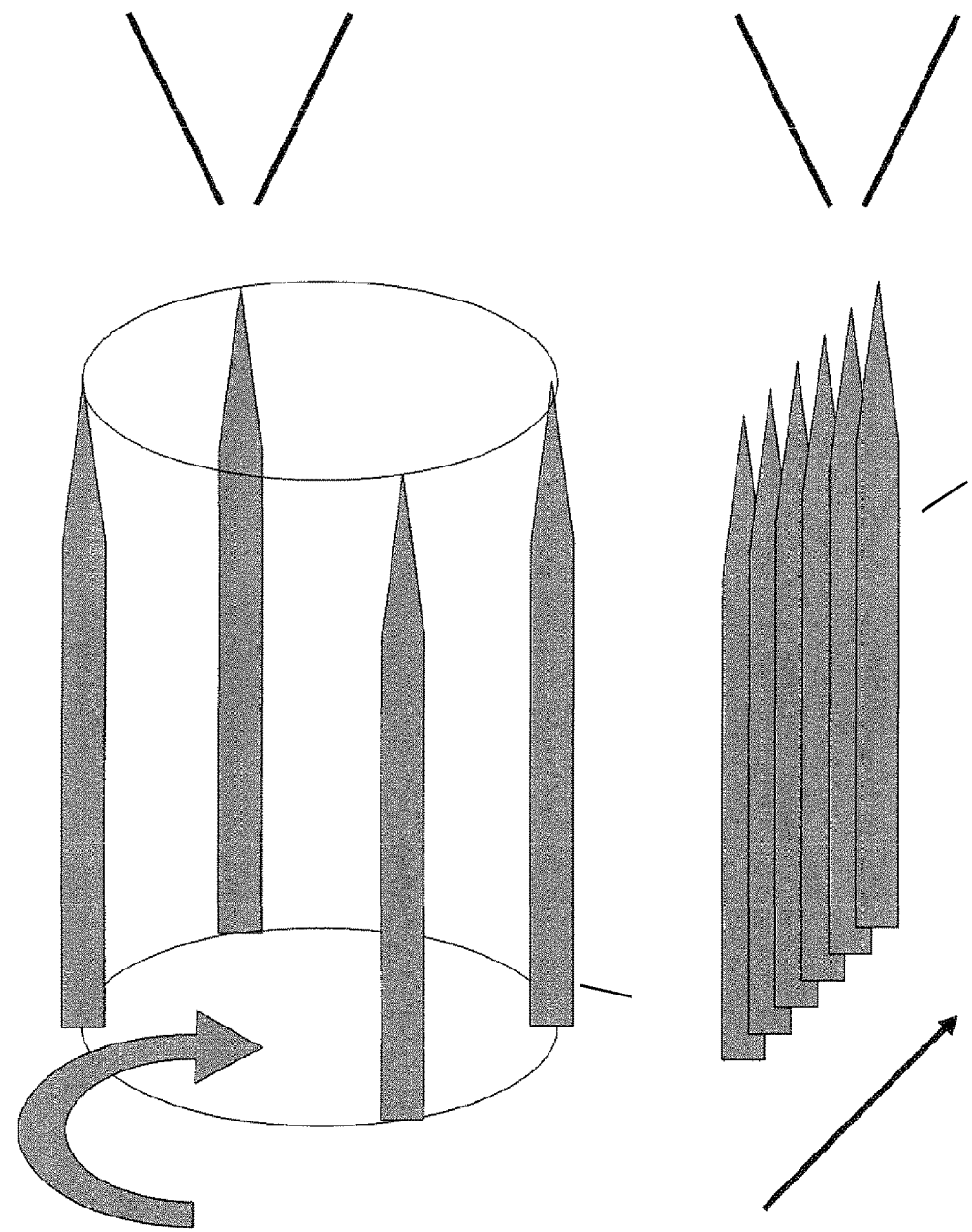
FIG. 32A illustrates a radial array for a plurality of inserts.
FIG. 32B illustrates a linear array for a plurality of inserts.

Shown in FIG. 4 is a block diagram example of a system to implement automated tubing connections utilizing a receiving hardware and compression system 10 and a plurality of "plug and play" insert devices 11 that will be subsequently compressed resulting in automated seals for the processing of fluid streams. Fluid, gas or liquid, may be provided by a fluid delivery system 12 integrated with the receiving hardware 10. The resulting transferred or processed fluid may then be delivered to fluid processing hardware or a detector system 13. The inserts 11 contain the necessary structures such as ferrules, receiving ports and materials necessary to seal the tubing and fluidic components to the receiving hardware 10. The inserts 11 may contain one more components for fluid processing and manipulation. Furthermore a plurality of inserts, present in either a serial or parallel fashion, may exist as shown in FIG. 32.

Figure 5:
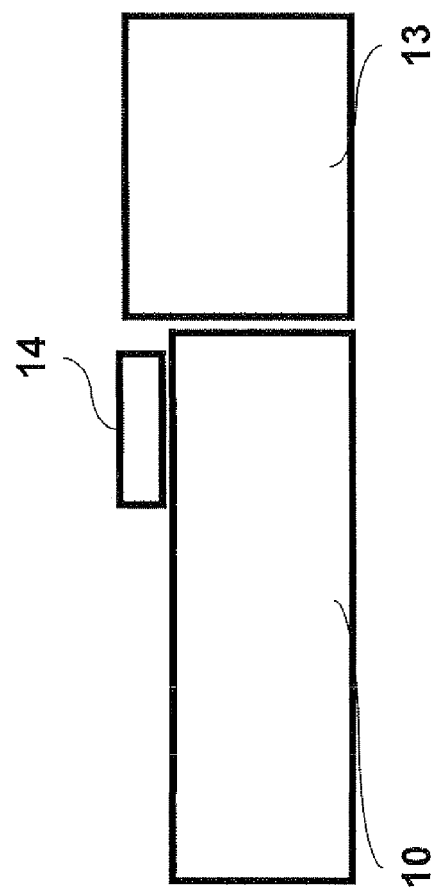
FIG. 5 is a block diagram of an insert containing a target sample of interest, the receiving compression hardware and the fluid processing hardware.

Shown in FIG. 5 is a block diagram example of a system to implement automated pressure connections utilizing a receiving hardware and compression system 10 and the "plug and play" sample/analyte containing at least one insert 14 (e.g., component containing instert(s) holding sample (liquid/gas/solid)). In this embodiment the sample/analyte containing insert 14 is interfaced via the receiving hardware and compression system 10 and the sample/analyte contained in the insert may be subsequently processed by the fluid processing hardware or detector system 13. The sample/analyte contained in the insert may be manipulated by pressure such as a pumping mechanism, vacuum, positive displacement, negative displacement, capillary force, pumping systems or the like. The sample/analyte containing inserts may be either disposable or reusable. The system may further operate as an autosampler injector system in conjunction with other fluid processing hardware or detector systems. When the insert is used only once, sample-to-sample cross-contamination is not possible as the sample/analyte is only exposed to the sample/analyte insert a single time. When the device is used only once, there is no risk of carry-over, leading to faster cycle times between sample analyses as there is no need for a washing cycle between samples. The insert is loaded with sample in a manual or automated fashion via positive or negative displacement. The sample loading or collection may occur either locally or remotely as part of a sampling system. In one embodiment the autosampler loads the sample into a high pressure sampling port having a compression connection of the present invention.

Figure 6:
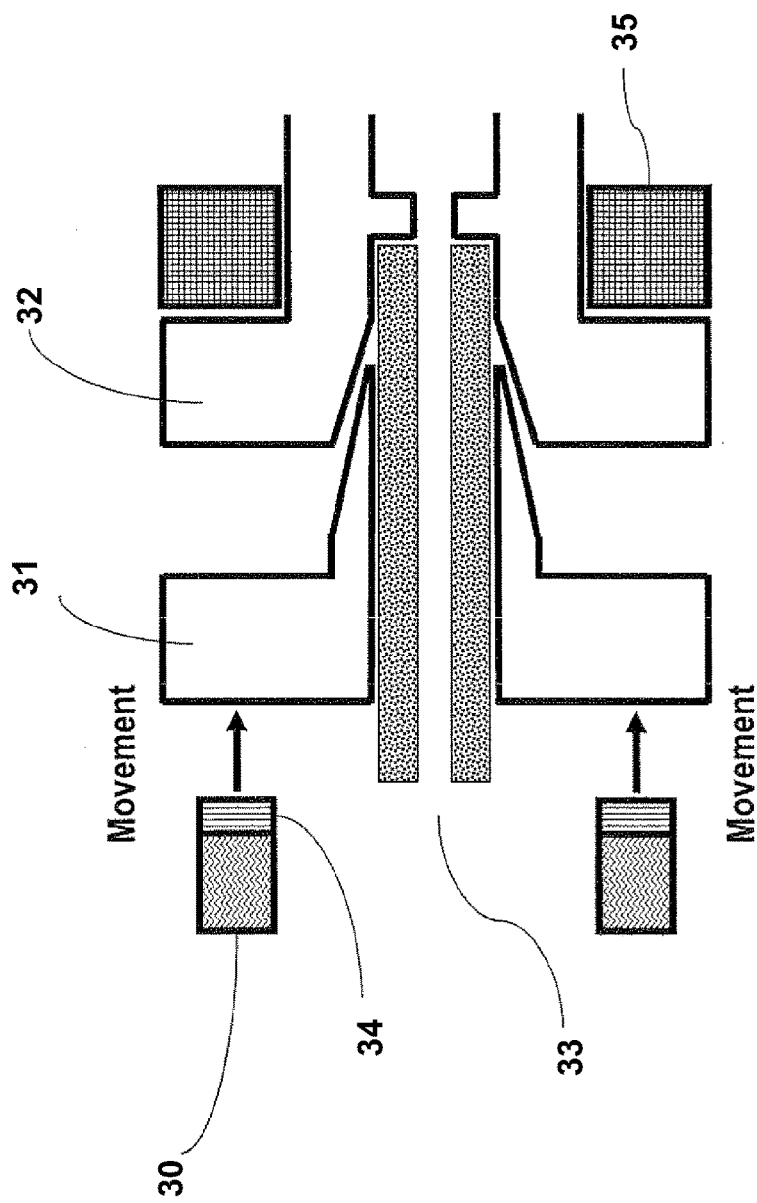
FIG. 6 is a cross-sectional view of a tube being sealed with a ferrule and receiving port via axial force generated by the controlled force compression system.

Shown in FIG. 6 is across-sectional view of an automated compression system and fitting components capable of making automated high and low pressure fluidic connections. The drive force compression hardware 30 supplies axial-directed driving force to the ferrule 31. The axial force compresses the tapered ferrule 31 against the tapered receiver port 32 (single-sided), which in turn effects a seal by creating a singular plane of contact around the circumference of the tube 33. The outer surface of the ferrule 31 and the inner surface of the receiver port 32 are both substantially smooth. The driving force mechanism may be applied by human intervention, or preferably, in an automated fashion by any device sufficient to provide a driving force such as, but not limited to, a mechanical lead screw, servo motor, pneumatic components, mechanical components, hydraulic components, spring mechanisms, or the like. The drive force does not cause rotational torque on the ferrule 31, receiver port 32, or tube 33. The drive force is controlled by a force measurement system in communication with the force measurement sensor 34. The receiving port 32 is supported by mechanical support structures 35 to prevent movement of the receiving port 32. The applied compression force is axial in nature and does not cause twisting or rotating of the ferrule or tube, thereby eliminating the risk of damaging the fragile tubing ends by grinding them against surfaces with which they come in contact. The driving force is measured by the force measurement sensor 34 that results in the accurate and precise readings of the driving force and ultimately the compression force applied. The force drive system is the system that receives force feedback from the force measurement sensor 34 and adjusts the force compression hardware 30 to exert the proper force on the compression system. The system allows for accurate and precise control of the fitting compression. The applied compression forces can be either static (fixed) or dynamic (programmable) to change the compression force over time as needed to form a proper sealing force. This accurate and precise control of both the drive mechanism and the force measurement eliminates the possibility of over compressing the fitting, which could cause leaking, cracking, and particle generation problems. The force measurement sensor can be a mechanical strain gage, piezoelectric sensor, transducer, load cell sensor, or resistance sensor. Additionally, the force measurement sensor can measure the direct or indirect force.

For a cylinder-based drive force systems, the applied force can be calculated indirectly by using the applied gas or hydraulic pressure and the cylinder diameter. The fluid pressure applied to the cylinder may be measured with an analogue or digital pressure sensor.

For a geared drive force system, such as a servo motor or a lead screw, the drive force may be indirectly determined by using the applied torque from the motor and the gearing parameters. Additionally a torque sensor may be placed in-line.

Direct measurement for any drive system may determined by placing an analogue or digital sensor in-line between the drive mechanism and the substrates to be compressed, such as an analog strain gage, a digital strain gage, or preferably, a load cell. The gage or load cell may be chosen for a given application range to provide an accurate and precise applied force measurement. The gage or load cell could also be present in a system to provide feedback for changing the applied force by the drive force measurement.

The connecting and fitting materials may be made of conductive, insulator, or doped materials including metals, metal mixtures or alloys, glass, ceramic, metal-semiconductor mixtures or alloys, polymers, conductive polymers, carbon or graphite, mixtures of carbon and polymers or plastics, organic compounds, elastomers, fluoropolymer, monomers, waxes, mixtures of inorganic-organic compounds and any combination thereof. It is understood that although the seal has been described as being made by a ferrule to receiver port connection, variations of the invention include compressing and sealing by cone, port-based, flatbottom, flanged, flangeless, or alike fitting ferrule combinations. The fittings can be of any shape or configuration and may include be part of an auxiliary device such as, but is not limited to, one or more inlets, outlets, transfer lines, traps, electrospray emitters, filters, frits, reactors, unions, tees, manifolds, mixers, vessels, injectors, adapters, back-pressure regulators, couplers, plugs, loops, needles, columns, pre-columns, nano-liquid chromatography columns, injector valves, check valves, metering valves, splitting valves, purge valves, switching valves, needles, Y-connecters, or other like fluidic components.

The connecters and fittings may be used in isolation or as part of a system. The fittings can be integrated into a hardware device or act as free standing connections.

Shown in FIGS. 7A and 7B is a cross-sectional view of an automated compression system and fitting components capable of making multiple, automated, high and low pressure fluidic connections. As shown in FIG. 7A, two separate tubes, 42 and 43, in communication with a dual-sided receiving port 41 are sealed via axial force generated by a single driving force compression system 44 with a mechanical support 45 preventing the movement of ferrule 47. The drive forces are controlled by the force drive system including force/load measurement hardware 48. As there is only a single drive force mechanism, both tubes 42 and 43 are sealed with equal compression force. All fittings in the axial plane of and between the single driving force compression system 44 the mechanical support 45 are compressed with the same force. The dual-sided receiving port 41 can move or "float" until each fitting is compressed or loaded against the mechanical supports 45. Thus altering the applied drive force would influence the compression force applied to all of the in-line components, for example ferrule 49. It is understood that multiple drive forces can be existed on the system to effect a seal.

Referring to FIG. 7B, there is shown an alternative embodiment with two separate tubes 42 and 43 in communication with a dual-sided receiving port 41 are sealed via axial force generated by a dual driving force compression system 46 with mechanical support 45 preventing the movement of the dual-sided receiving port 41. The drive forces are controlled by the force drive system. The dual-sided receiving port 41 is fixed in place by mechanical supports 45. Thus, the compression force applied to the fittings and tubes on each side of the receiver port can be independently controlled. This allows for compression to be applied independently to a specific fitting, which can be incorporated into a larger array or a plurality of fittings. This independence allows for individual components within a system to be compressed and released solitarily, allowing for automated changing of specific components without changing the compression of other fittings.

Referring to FIG. 8A, there is shown across-section of an insert containing multiple components including: ferrules 31, receiver ports 51, capillary tubes 52, and a floating mechanical structure 53 in the insert housing 54. Ferrules, receiver ports, and fitting components are integrated within the internal structure of the insert. Once the insert is placed in the receiving hardware, a single driving force compression system 44 is applied to one end of the insert while the opposing insert end is constrained by mechanical supports 45. The compression force generated in this manner is transferred to all components, ferrules, and receiving ports present in the array, as the insert contains a floating structure which transfers force to all components within the insert. In this manner, sealing of multiple tubes within the insert is achieved, using a single axial drive force. The floating mechanical structure 53 allows components to be separated or located in distinct regions of the array. It is understood that although a linear structure is shown, other off-axis geometries are applicable. The drive force is controlled by the force drive system.

Referring to FIG. 8B, there is shown a cross-section of an insert containing multiple components: including: ferrules 31, receiver ports 51, capillary tubes 52, and a fixed mechanical support 55 in the insert housing 54. Ferrules, receiver ports, and fitting components are integrated within the internal structure of the insert. The insert also contains a structure that is a fixed mechanical support 55 which remains stationary when force is applied by the dual driving force compression system 46. Once the insert is placed in the receiving hardware, two independently operated axial drive forces are applied to each end of the insert. The component fittings, ferrules, and receiver ports are compressed against the fixed mechanical support 55 contained within the insert. Fittings on either side of the fixed mechanical support may be compressed and sealed with independent force as applied by each drive force mechanism of the dual driving force compression system 46. Sealing of multiple tubes within the insert is achieved. The fixed mechanical support 55 may be affixed to the insert itself or may be locked in place relative to the receiving hardware. It is understood that although a linear structure is shown, other off-axis geometries are applicable. The drive force is controlled by the force drive system.

Figure 9:
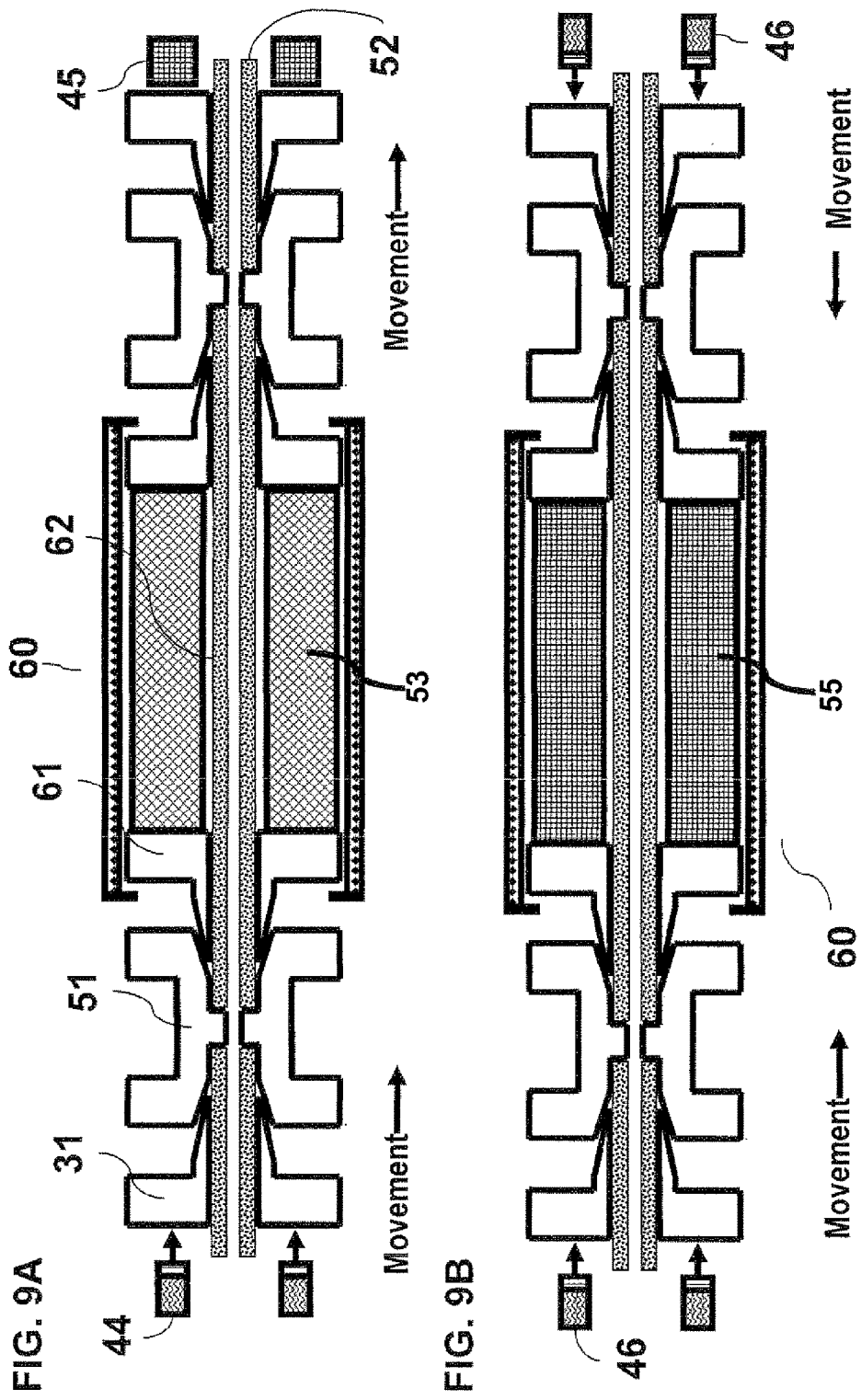
FIG. 9A is a cross-sectional view of an assembly of ferrules and receiving ports where part of the assembly is contained within the insert, the column is sealed to two separate tubes which are external to the insert.
FIG. 9B is a cross-sectional view of an assembly of ferrules and receiving ports where part of the assembly is contained within the insert, the column is sealed to two separate tubes which are external to the insert, separate controlled force compression systems, independently compress all of the ferrules and receiving ports on the inlet and outlet sides, allowing for independent sealing control and compression strength.

Referring to FIG. 9A, there is shown a cross-sectional view of an assembly of component fittings, where the insert 60 houses only some of the components, and a single driving force compression system 44 is employed to generate the compression sealing force both internally and externally to the insert 60. Integrated within the insert are ferrules 61, tubes 62, and the floating mechanical structure 53. External to the insert and part of the receiving hardware are ferrules 31, receiving ports 51, and tubes 52. Once the insert is placed in the receiving hardware, the single driving force compression system 44 applies driving force to one end of the assembly, while the opposing end is constrained by mechanical supports 45. The compression force generated in this manner is transferred to all in-line fitting components contained between the single driving force compression system 44 and the mechanical supports 45. It is understood that the insert can contain any number of tubes, columns, reactors, or any other device desirable in chromatographic and fluidic applications.

Referring to FIG. 9B, there is shown is a cross-sectional view of an assembly of component fittings, where the insert 60 houses only some of the components, and the dual driving force compression system 46 is employed to generate the compression sealing force both internally and externally to the insert 60. Integrated within the insert are ferrules 61, tubes 62, and the fixed mechanical support 55. External to the insert and part of the receiving hardware are ferrules 31, receiving ports 51, and tubes 52. Once the insert is placed in the receiving hardware, the dual driving force compression system 46 applies axial force independently to each end of the component assembly. The component fittings, ferrules, and receiver ports are compressed against the fixed mechanical support 55 contained within the insert. Fittings on either side of the fixed mechanical support 55 may be compressed and sealed with independent force as applied by each end of the dual driving force compression system 46. The fixed mechanical support 55 may be affixed to the insert itself or may be locked in place relative to the receiving hardware. It is understood that the insert can contain any number of tubes, columns, reactors, or any other device desirable in chromatographic and fluidic applications.

Shown in FIG. 10A is a cross-sectional view similar to FIG. 9A of an assembly of component fittings, where the insert 60 houses only some of the components, and a single driving force compression system 44 is employed to generate the compression sealing force both internally and externally to the insert 60. In one embodiment the insert houses a column and a spray emitter.

Shown in FIG. 10B is a cross-sectional view similar to FIG. 9B of an assembly of component fittings, where the insert 60 houses only some of the components, and a dual driving force compression system 46 is employed to generate the compression sealing force both internally and externally to the insert 60. In one embodiment the insert houses a column and a spray emitter.

Figure 10C:
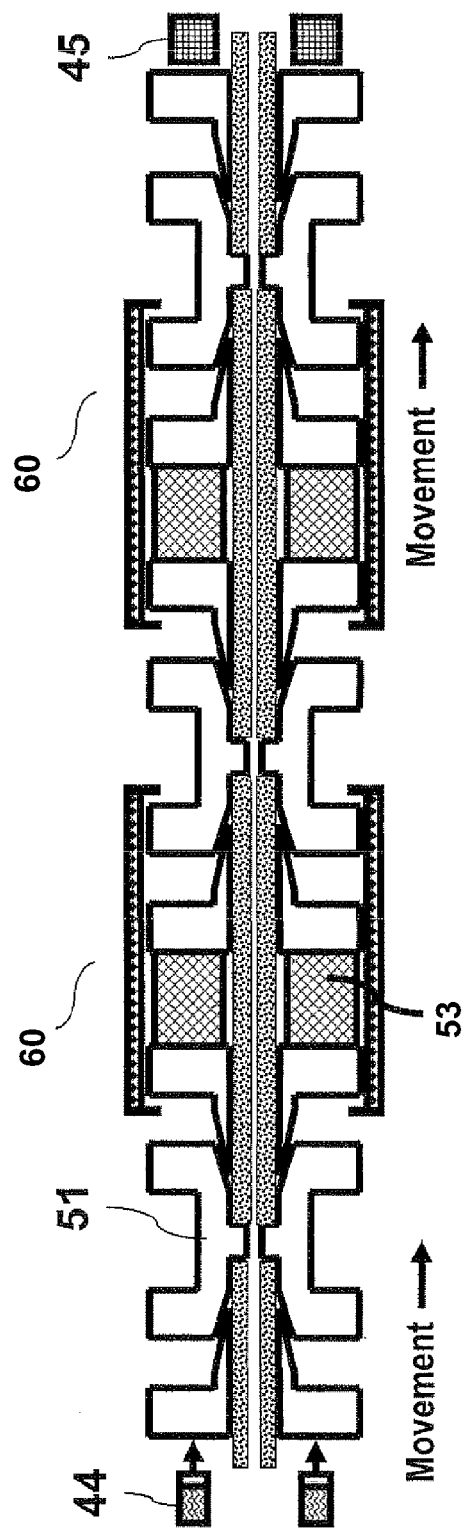
FIG. 10C is a cross-sectional view of an assembly of fittings where part of the assembly is contained in a first insert and part of the assembly is contained in a second insert.

Shown in FIG. 10C is a cross-sectional view of a fitting assembly. The assembly contains a plurality of inserts 60 in-line with the driving force. The compression force is transferred to all in-line fitting components. It is understood that any number of inserts may be linked together and any number of fittings may be placed between inserts. Although a single driving force compression system is shown it is further understood that a dual driving force compression system may be used without departing from the scope of the invention. In one embodiment each insert contains a single tube, pre-column, column, reactor, spray emitter, or other device desirable in chromatographic and fluidic applications. It is understood that many inserts can be sealed, end-to-end, in a tandem fashion.

Figure 11:
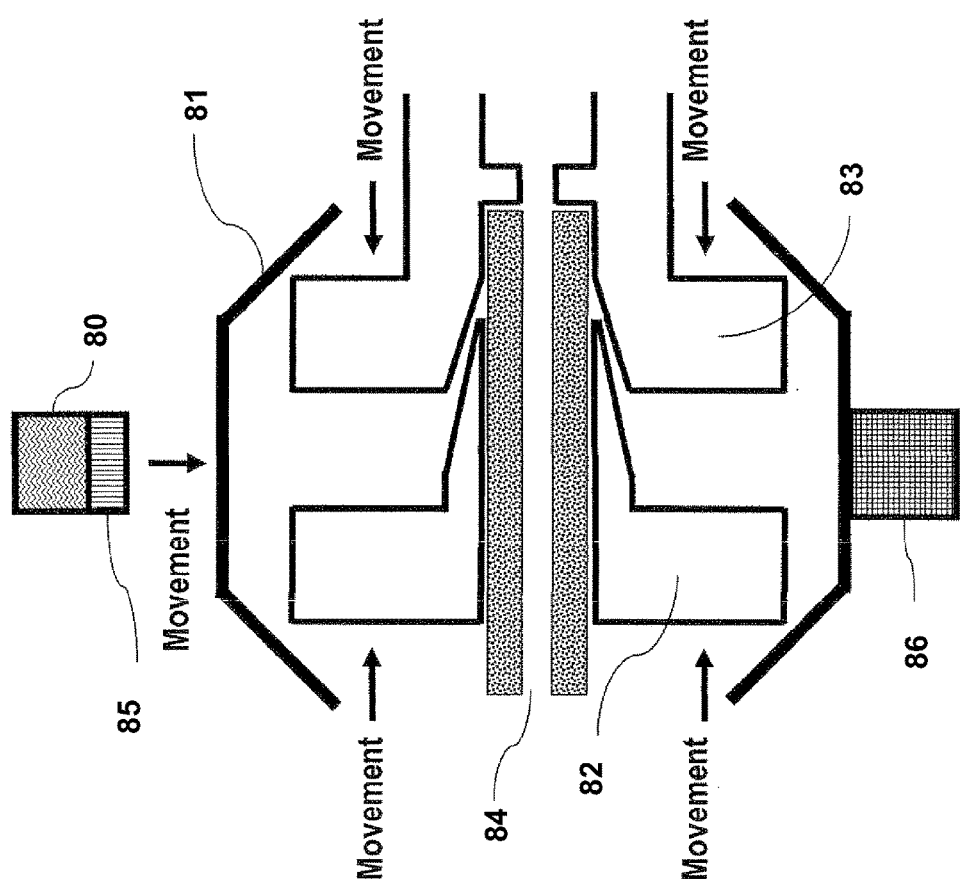
FIG. 11 is a cross-sectional view of a tube being sealed with a ferrule and receiving port via radial movement of the controlled force compression system, and this movement subsequently generates axial sealing force.

Shown in FIG. 11 is a cross-sectional view of an automated compression system and fitting components capable of making automated high and low pressure fluidic connections. The driving force compression hardware 80 supplies radial directed driving force relative to the ferrule 82 and receiving port 83. An angled, clamping structure 81 pushes and squeezes the outer edges of the ferrule 82 and receiving port 83, subsequently generating axial directed force. The translated axial force compresses the tapered ferrule 82 against the tapered receiver port 83, which in turn affects a seal by creating a singular plane of contact around the circumference of the tube 84. A mechanical support structure 86 prevents movement of one of the clamping structures 81. The drive force is controlled by a force measurement system in communication with the force measurement sensor 85. The applied compression force is axial in nature and does not cause twisting or rotating of the ferrule or tube, thereby eliminating the risk of damaging the fragile tubing ends by grinding them against surfaces with which they come in contact. The driving force is measured by the force measurement sensor 85 which results in accurate and precise readings of the driving force and ultimately the compression force applied. The drive force system is an automated system with feedback from the force measurement sensor 85 controlling the drive force compression hardware 80. The system allows for accurate and precise control of the fitting compression. The applied compression forces can be either static (fixed) or dynamic (programmable) to change the compression force over time as needed to form a proper sealing force. This accurate and precise control of both the drive mechanism and the force measurement eliminates the possibility of over compressing the fitting, which could cause leaking, cracking, and particle generation problems. It is understood that a drive force may be applied to each clamping element. It is further understood that the clamping elements may take any shape capable of generating an axial compressing force, and the clamping elements may be of differing shapes.

Figure 12:
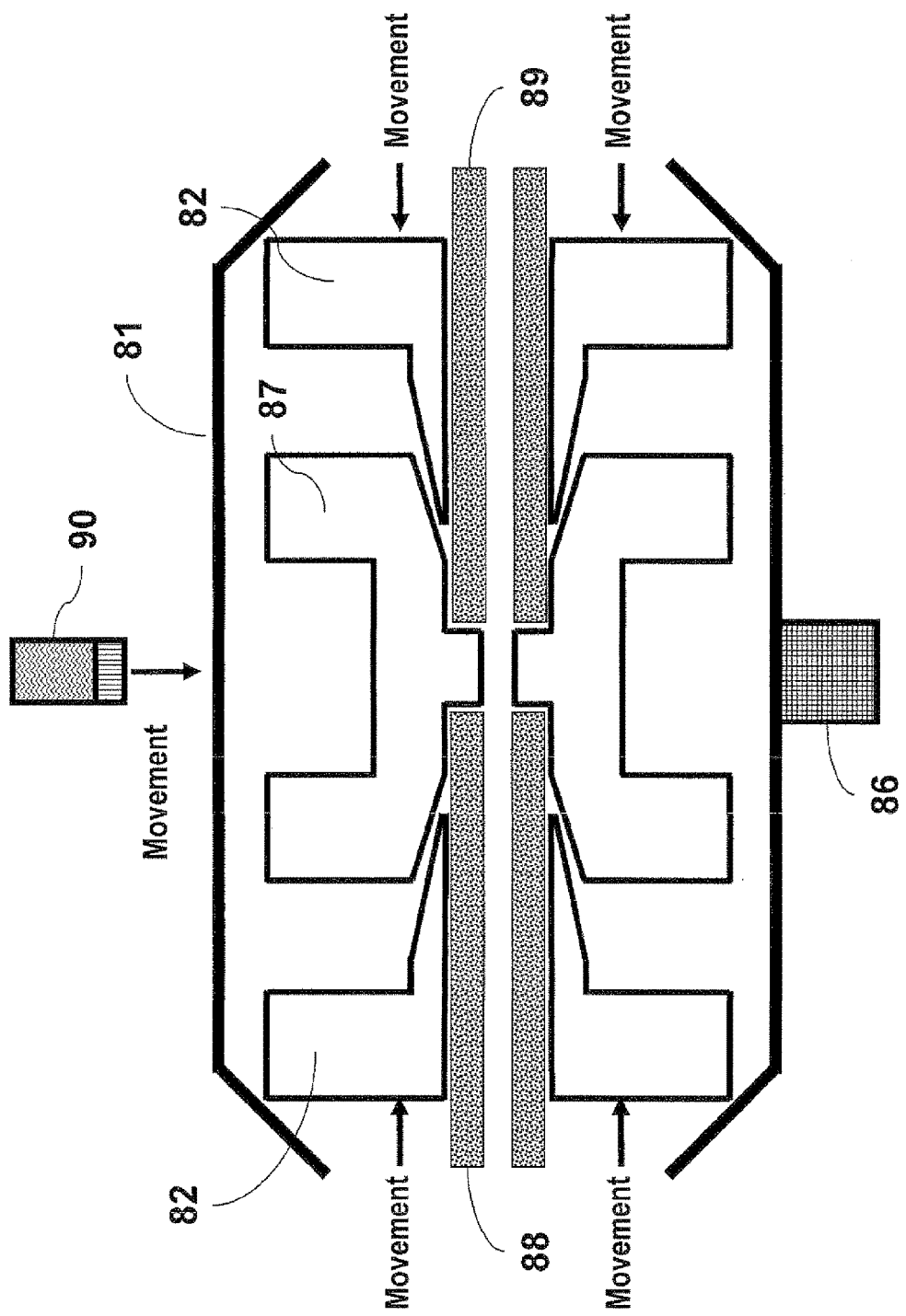
FIG. 12 is across-sectional view of a dual-sided receiving port where two separate tubes are sealed together with ferrules and receiving port via radial movement of the controlled force compression system, and this movement subsequently generates axial sealing force, the tubes are sealed with equal force as there is only a single compression system.
Figure 13:
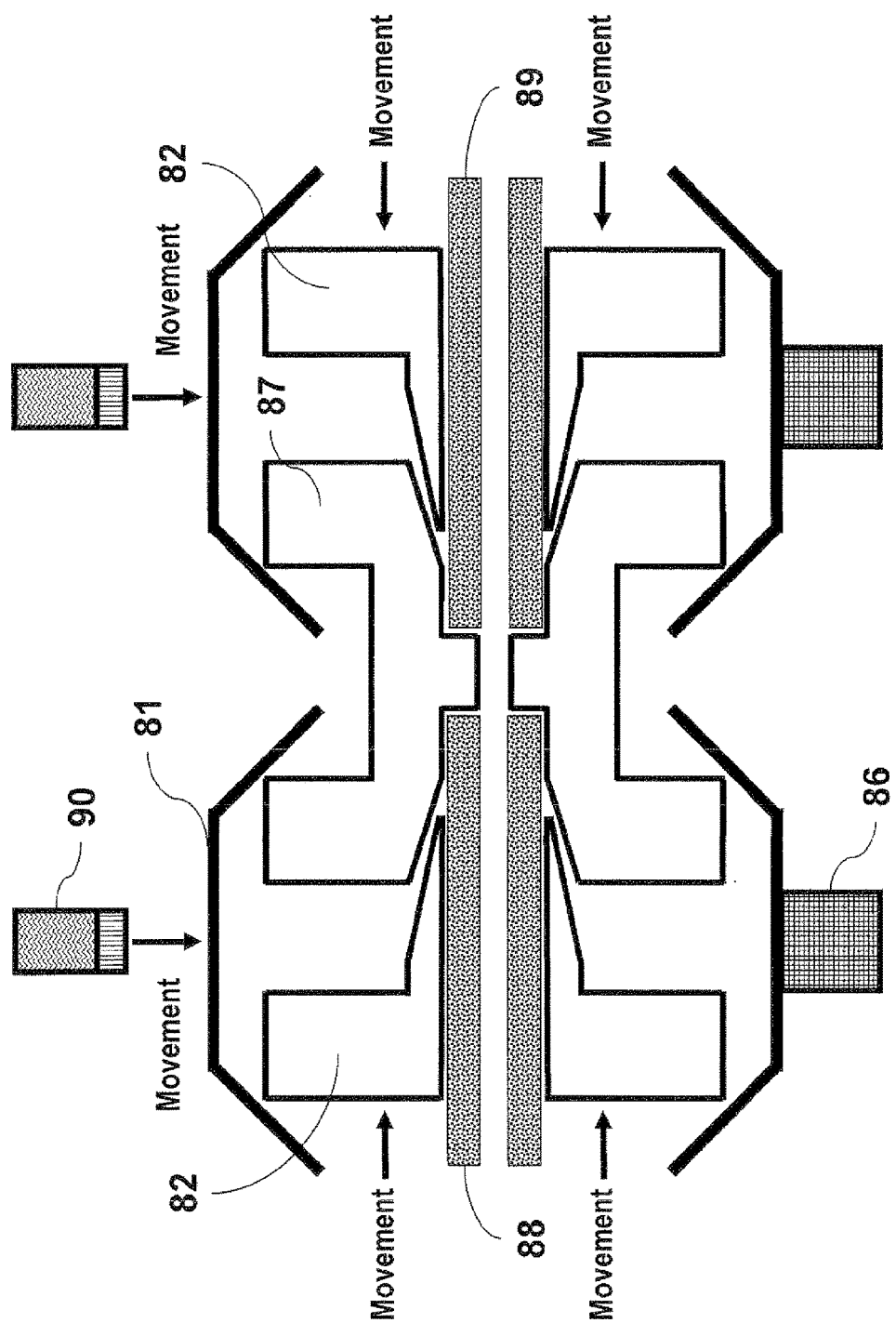
FIG. 13 is a cross-sectional view of a dual-sided receiving port where two separate tubes are sealed together with ferrules and a receiving port via radial movement of the controlled force compression system, and this movement subsequently generates axial sealing force, the tubes have independent sealing forces as there are two independent compression mechanisms and the receiving port is braced.

Shown in FIGS. 12 and 13 are cross-sectional views of automated compression systems and fitting components capable of making multiple, automated, high and low pressure fluidic connections. FIGS. 12 and 13 show a dual-sided receiving port 87 where two separate tubes 88 and 89, are sealed via radial drive force movement, and this movement is subsequently converted to axial force generated by a driving force compression system 90. The drive force is controlled by the force drive system.

Referring to FIG. 12, both tubes 88 and 89 are sealed with equal compression force as there is only a single drive force employed. The drive force is generated in the radial plane which is then mechanically converted to axial directed force by an angled, clamping structure 81 which pushes and squeezes the outer edges of the ferrule 82 and receiving port 87. All fittings between the angled clamping structures are compressed, thus a plurality of seals may be made by the single drive force mechanism. Altering the applied drive force changes the compression force applied to all of the components contained within the angled, clamping structure 81.

Referring to FIG. 13, tubes 88 and 89 are sealed using two independent clamping elements 81. Each side of the two-sided receiving port 87 has an independent drive force with a corresponding angled, clamping structure 81 and a ferrule 82. Each clamping element 81 may independently push and squeeze the outer edges of the corresponding ferrule 82 and receiving port 87, subsequently generating axial directed force. The application of two distinct drive forces and two clamping elements allows for the compression force applied to the fittings and tubes on each side of the receiver port to be independently controlled. This allows for compression to be applied independently to specific fittings which are incorporated in a larger array or a plurality of fittings. This independence would allow for individual components within a system to be compressed and released solitarily, allowing for automated changing of specific components.

Figure 14:
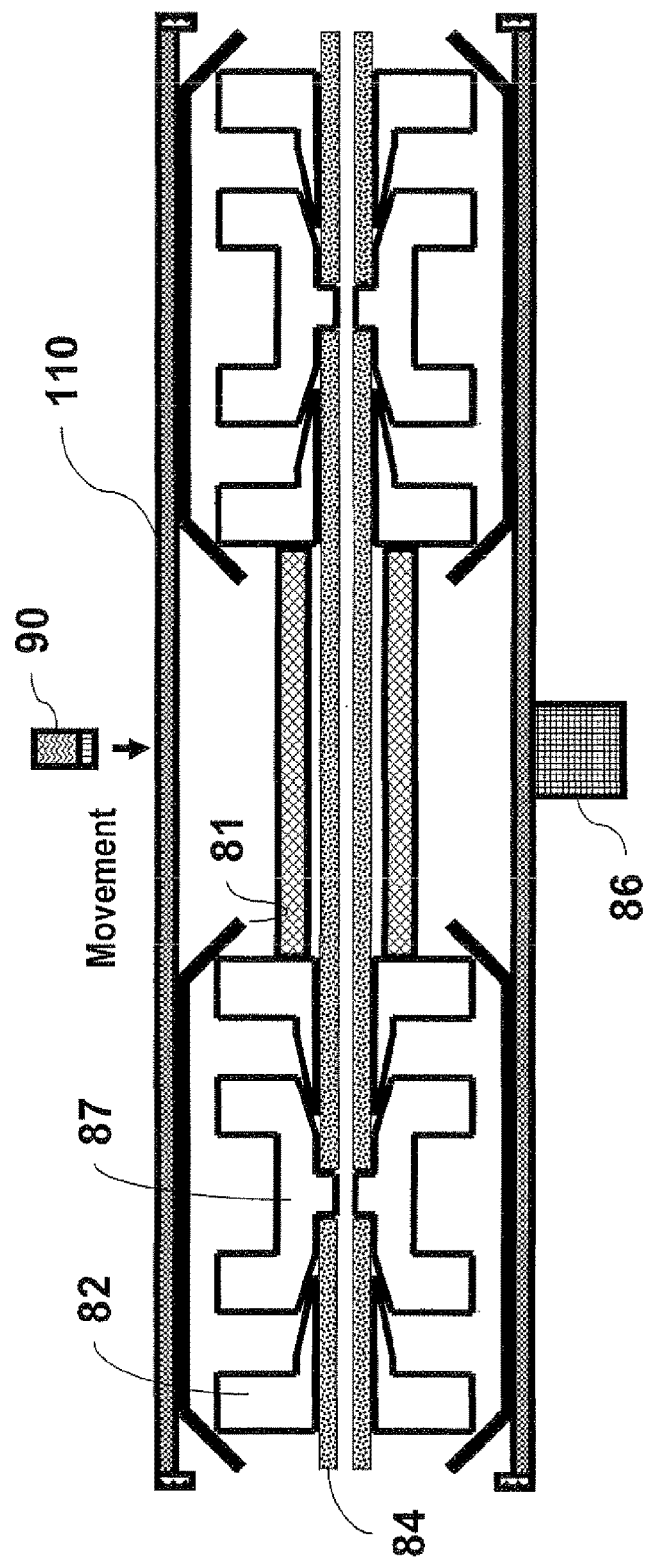
FIG. 14 is a cross-sectional view of an assembly of ferrules and receiving ports in an insert where a column is connected to two separate tubes at its inlet and outlet locations, radial movement of the controlled force compression system subsequently generates axial force which seals all the components.

Referring to FIG. 14, there is shown a cross-sectional view of an assembly of fittings present in an insert. Ferrules 82, receiving ports 87, tubes 84, clamping structures 81, and structural housing 110 are all contained in the insert. Here a single drive force applies radial force to the rigid structural housing 110 of the insert. This radial drive force in turn pushes two angled, clamping structures 81 which convert the radial drive force applied into axial force. Here a single radial drive force is applied to two angled, clamping structures, however a single radial drive force could be applied to many angled, clamping structures, making many compression connection seals.

Figure 15:
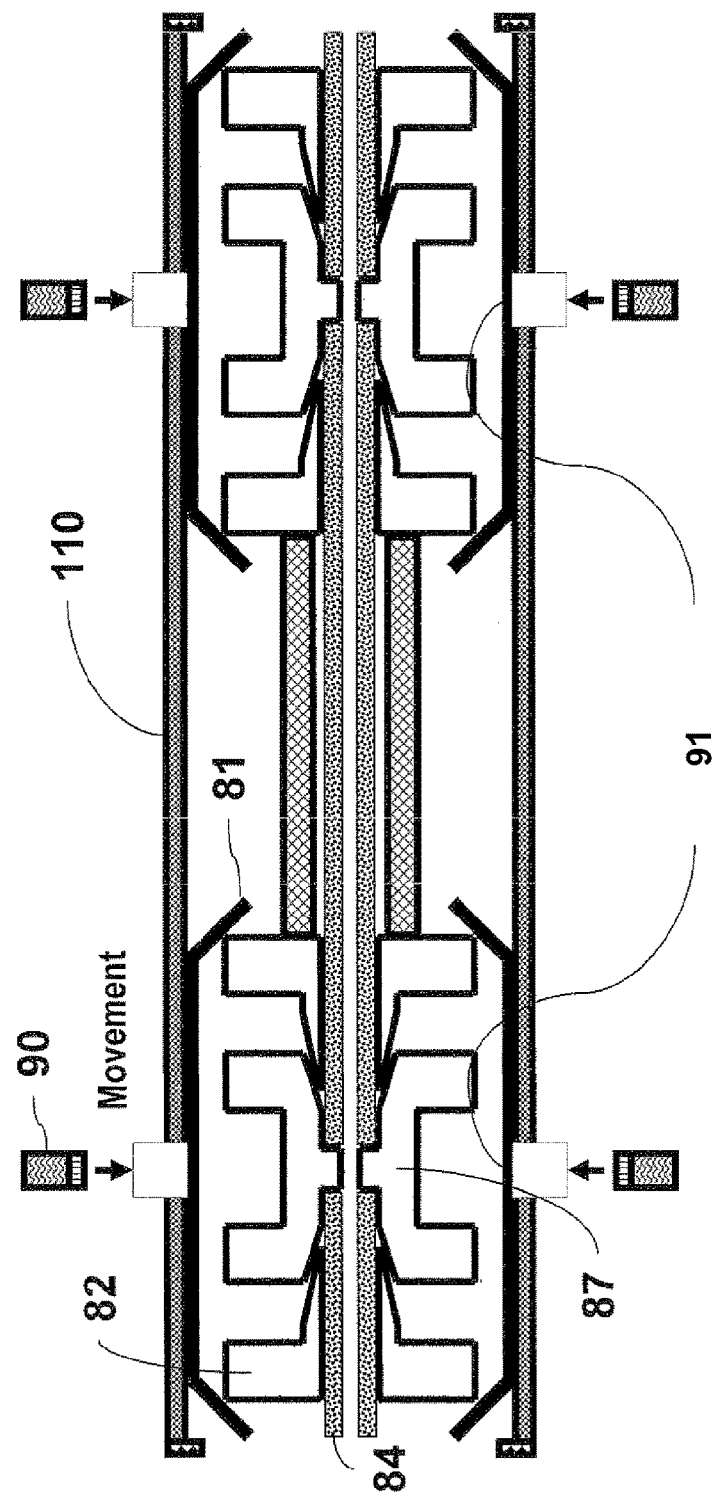
FIG. 15 is a cross-sectional view of an assembly of ferrules and receiving ports in an insert where a column is connected by two separate tubes at the inlet and outlet locations, independent radial movement of two controlled force compression systems produce subsequent axial force, sealing both the inlet and outlet ends independently.
Figure 16:
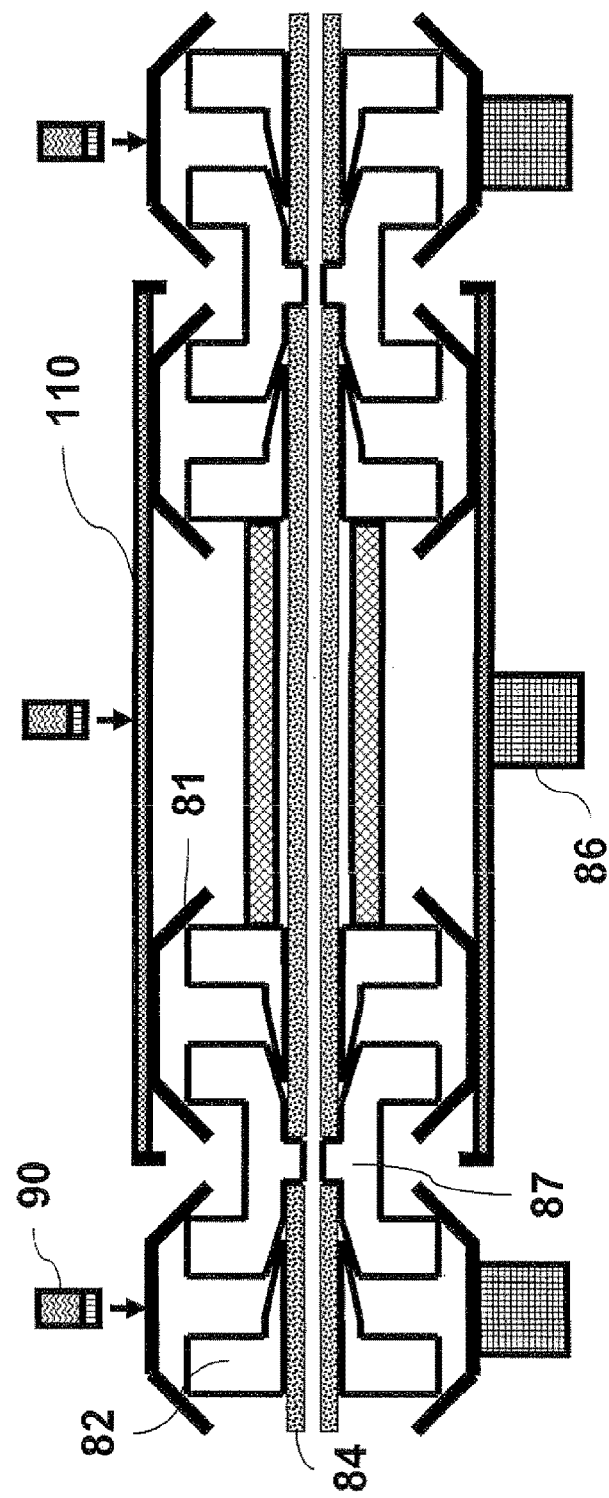
FIG. 16 is a cross-sectional view of an assembly of ferrules and receiving ports where part of the assembly is contained within the insert, the column is sealed to two separate tubes, both of which are external to the insert, and independent radial movement of three controlled force compression systems produce subsequent axial force, compressing and sealing the components.

Shown in FIG. 15 is a cross-sectional view of an assembly of fittings present in an insert. Ferrules 82, receiving ports 87, tubes 84, clamping structures 81, and structural housing 110 are all contained in the insert. Here two drive force mechanisms 90 apply radial force through openings 91 to the rigid housing structure of the insert. Each radial drive force in turn pushes a corresponding angled, clamping structure which converts the radial drive force applied into axial force. Each radial drive force is operated independently which allows the axial compression force generated by each clamping structure 81 to be independently controlled. Each radial drive force mechanism and its corresponding clamping structure are shown to make two seals. In a similar manner, if the angled, clamping structure only spanned a ferrule and receiving port (as shown in FIG. 16) then single seals could be independently controlled. Although radial drive force mechanisms are shown on both sides of the insert housing it is understood that drive force mechanisms could be present on a single side and push against mechanical supports opposite them as both embodiments allow for a radial, squeezing force to be generated.

FIG. 16 is a cross-sectional view of an assembly of fittings, some of which are present in the insert. Ferrules 82, receiving ports 87, tubes 84, clamping structures 81, and structural housing 110 are all contained in the insert. External to the insert are additional ferrules, receiving ports, and tubes. A plurality of drive forces apply radial forces. Two radial drive forces are directly applied to clamping structures 81 exterior to the insert. In both cases the angled, clamping structure converts the radial drive force into axial force which generates a compression seal. Here each drive force external to the insert makes a single compression seal. If the clamping structures spanned more than a single fitting, more seals could be made by a single drive force. A third drive force applies radial force to the rigid housing 110 of the insert. The insert contains multiple clamping structures 81 so when radial force is applied by the drive force mechanism, the force is applied all along the rigid insert housing and subsequently is applied to the multiple angled, clamping structures. The angled, clamping structures convert the radial force to an axial force, which in turn creates compression seals between the fitting components.

Figure 17:
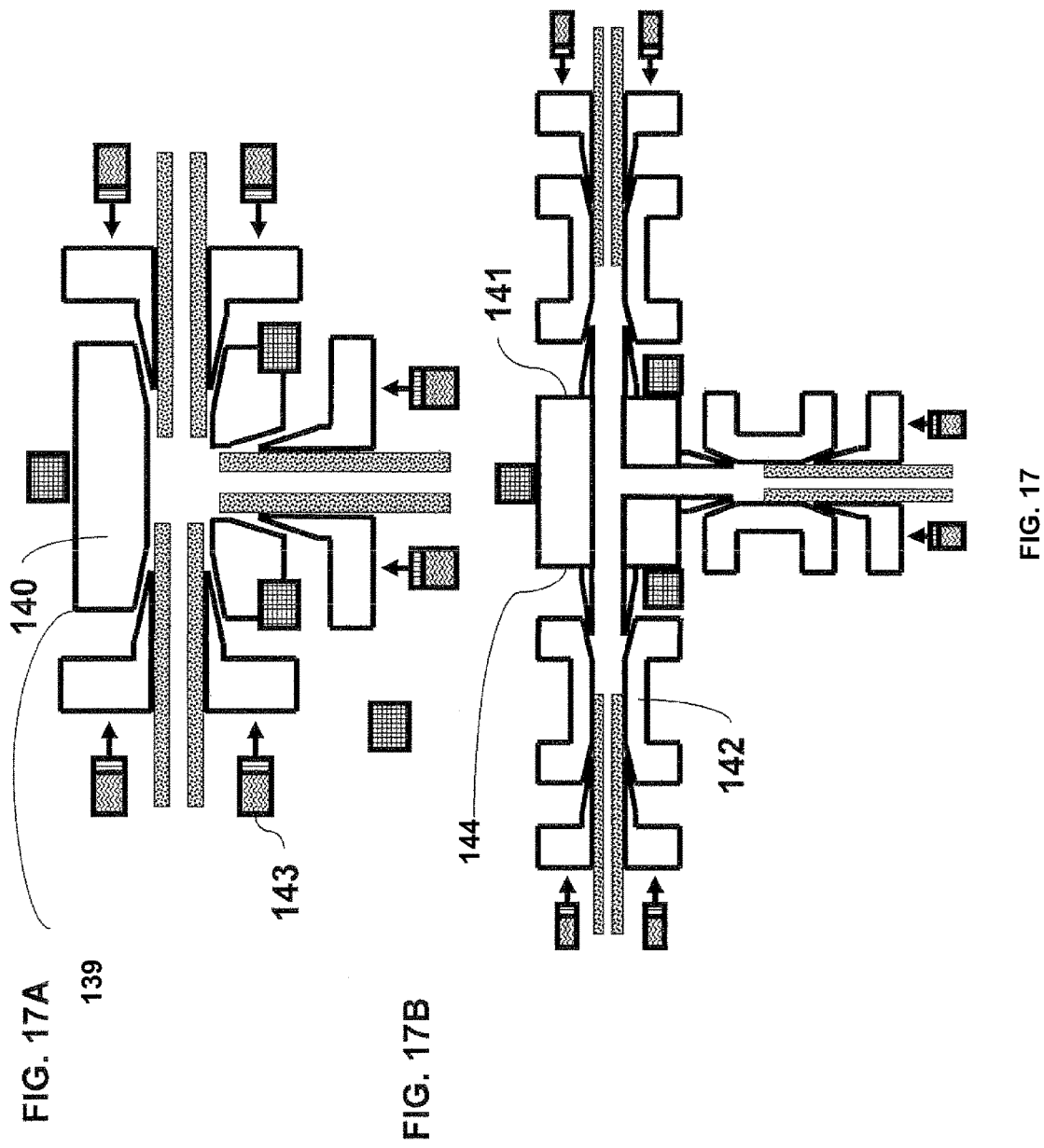
FIG. 17A is a cross-sectional view showing a Tee structure with female ends where three ferrules are engaged with a three-way receiver port using three independently controlled force compression systems.
FIG. 17B is a cross-sectional view showing a Tee structure with ferrule-like outlets where the three outlets of the Tee are engaged with three corresponding receiver ports using three independently controlled force compression systems.

Shown in FIG. 17A is a cross-sectional view of a three-channel connector 139 employing the "plug-and-play" system having female receiving port connector ends 140 for interfacing with three corresponding ferrules. Alternatively, shown in FIG. 17B, the three-channel connector 144 having male ferrule connector ends 141 for interfacing with three corresponding receiver ports 142. In both embodiments, each corresponding ferrule/receiving port union at each channel is individually compressed by an axial driving force compression system 143. This force can be applied by either individual drive force mechanisms or by a single system that addresses the three channels. The three channel structure may act as a tee, mixer, manifold, or reactor.

Figure 18:
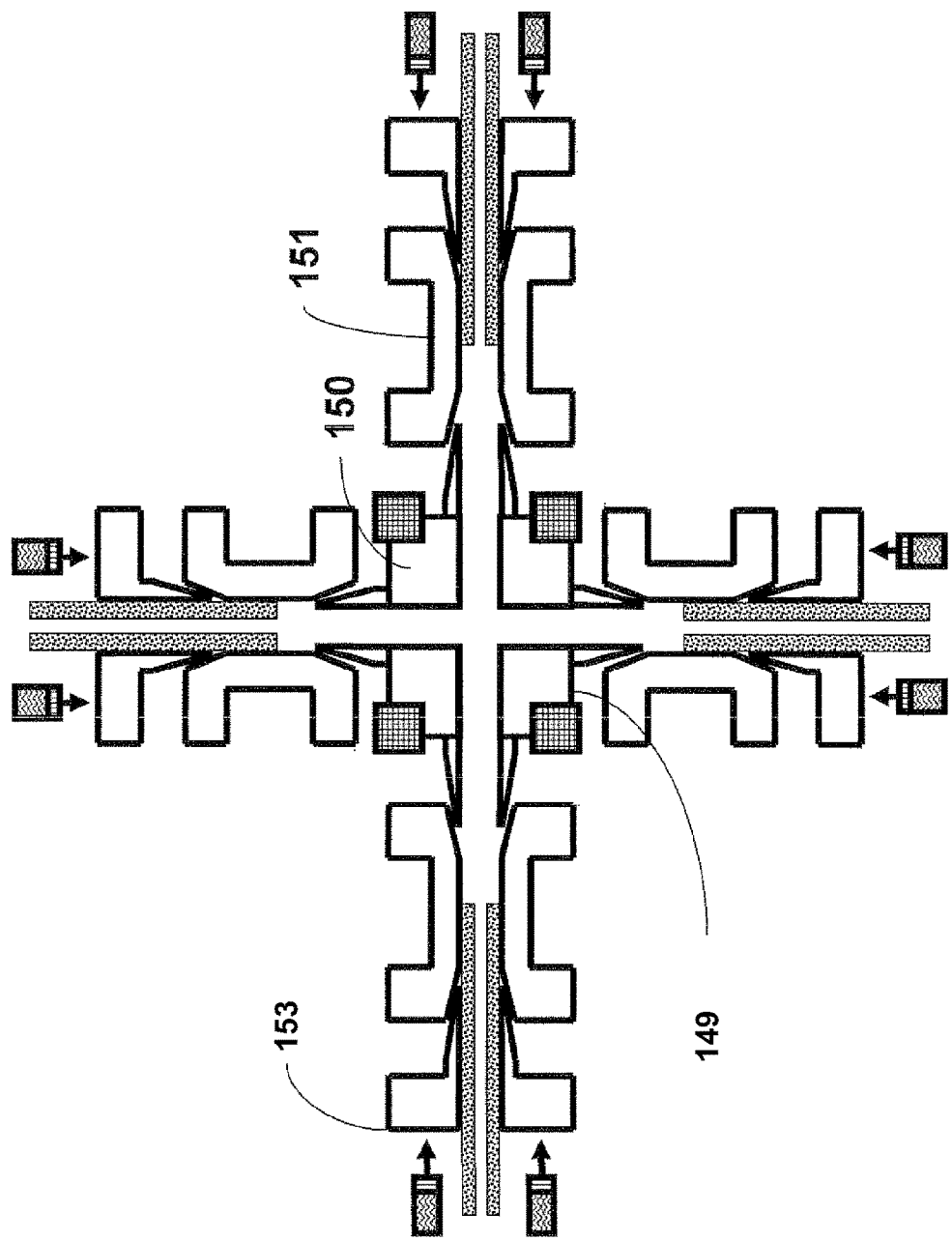
FIG. 18 is a cross-sectional view showing a manifold with four ferrule-like outlets where the four outlets of the manifold are engaged with four corresponding receiver ports using four independently controlled force compression systems.

Shown in FIG. 18 is a cross-sectional view of a four-channel connector 149 structure having male ferrule connector ends 150 for interfacing with four corresponding receiver ports 151. Alternatively, the connector ends could be female receiving port ends and interface to ferrules or a combination of male ferrule and female receiving port ends. The "plug-and-play" technology is employed to make the connections of the ports. Each ferrule 153/receiving port union at each channel is compressed using axial drive force movement. This force can be applied by individual drive force compression systems or by a single system that addresses all the four channels. The four channel structure may act as a tee, union, mixer, manifold, or reactor. It is understood that structures with additional channels can be employed.

In an alternative embodiment the "plug-and-play" compression fitting connection is used to connect any type of tube or fluidic component to a conventional multi-port valve used to redirect fluid streams. These valves are commonly referred to as switching valves. Compression fitting connections are made to one or more of the valve ports. A port on the switching valve serves as the receiver port in the compression connection. The valve is fixed to the docking station via a mechanical support. There are corresponding drive force systems for each port of the switching valve having a compression fitting connection. Alternatively the valve is mounted to traditional hardware and has an integrated force drive system.

Figure 19:
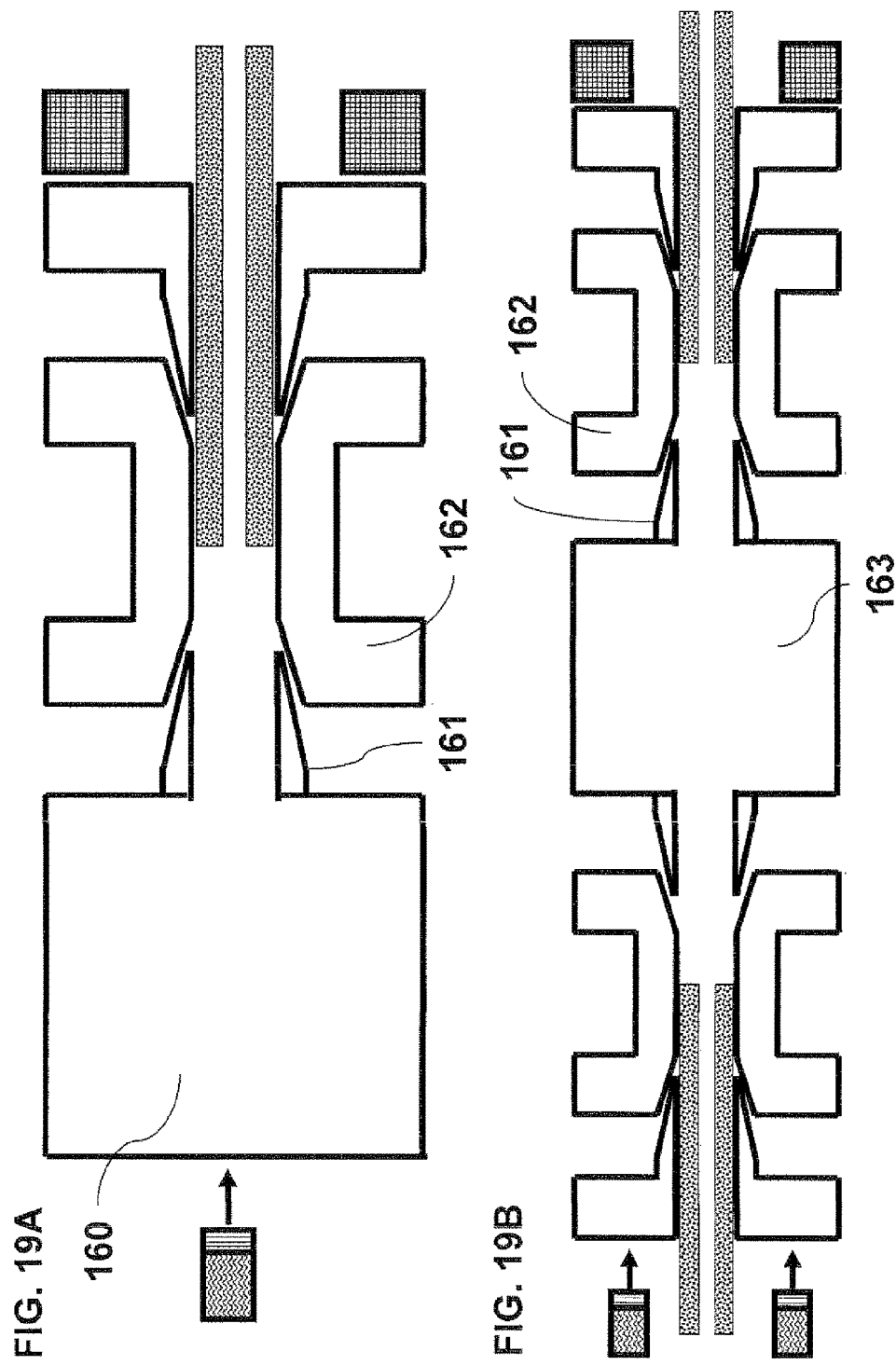
FIG. 19A is a cross-sectional view of a single orifice vessel having a ferrule-like opening which can seal against a receiver port system when axial force is generated by a controlled force compression system.
FIG. 19B is a cross-sectional view of a multi-orifice vessel having ferrule-like openings which can seal against receiver ports when axial force is generated by a controlled force compression system.

Referring to FIGS. 19A and 19B, there are shown cross-sectional views of fluid (gas or liquid) containing vessels where the fluid is a target sample of interest. The vessel is pre-filled with a sample, analyte, reactant, etc. and is then interfaced to an analysis system using "plug-and-play" technology. Delivery of the fluid sample to the analysis system may be via displacement using positive or negative pressure.

Shown in FIG. 19A is a cross-sectional view of a single orifice vessel 160 having a ferrule 161 around the opening which can seal against a receiver port 162 system by axial drive force movement. The vessel 160 may contain a target sample of interest that can be manipulated with positive or negative pressure.

Shown in FIG. 19B is a cross-sectional view of a multi-orifice vessel 163 having ferrules 161 around each of the openings which can seal against receiver ports 162 when axial force is generated by a controlled axial drive force movement. The vessel may contain a target sample of interest that can be manipulated with positive or negative pressure.

A gaseous target sample is collected into a sample vessel from an external system that either injects the vessel with sample, or pulls sample into the vessel using a vacuum. For example, the vessel could contain one or more ports (not shown), in addition to the one or more entrances or exits. The ports and entrance/exit openings may contain check valves, septa, or plugs to constrain/seal the gas in the vessel. A pump may be connected to one such port, applying vacuum to the vessel and thereby pulling gaseous sample into the vessel through an additional open port.

In an alternative embodiment, the vessel is pre-evacuated prior to use. At the time of sample collection, the vessel port is opened via a valve or alternatively pierced, if designed with a septum-like mechanism. The gaseous sample is pulled into the vessel due to the pressure differential. Once the sample has been collected, the entry/sampling port is either closed in the case of the valve, or re-sealed in the case of the septum.

In one embodiment the vessel acts as a simple storage vessel, or contains a material for trapping desired components, or analytes. The trapping material may be metal, plastic/polymeric, ceramic, solid phase extraction material, chromatographic media, particle, monolith, or a membrane support structure. The vessel also acts to store and protect the sample from the environment until its use. The vessel may be insulated or thermally conductive if maintaining constant temperature is desired. The gaseous sample is pulled or swept by the trapping material, which is integrated in the insert, during sample collection. Once the sampling has occurred, the vessel insert is placed into the receiving hardware. Compression connections are made prior to sample processing and analysis. The gaseous sample and/or the trapped sample components are delivered to the gas processing hardware or detector, such as a gas chromatograph, ion mobility instrument, or mass spectrometer. The sample delivery is achieved by pressurizing the vessel, or by evacuating the vessel. This is accomplished by a separate port or a common port with multiple access openings.

In an alternative embodiment, the vessel is also heated to release trapped components on the trapping structure integrated in the vessel. Alternatively, the trapping structure is removed from the vessel and placed in a different plug-and-play insert with additional components.

The plug-and-play vessel allows for automated sampling of gases. A sampling robot first "loads" the vessel, and then the vessel is transferred to processing hardware. The plug-and-play system is interfaced to this processing/detector hardware. The vessel insert is placed into the receiving hardware, the compression connections are made, and then the sample within the vessel is transferred to the processing/detector hardware in an automated fashion. In one embodiment the vessels are used in remote sampling applications, such as for chemical detection applications. Subsequently samples are collected into the insert vessels at a location remote from the receiving hardware and fluid processing equipment.

Liquid samples are collected into a sample vessel with two openings, as shown in FIG. 19B. The vessel is introduced to the target sample of interest in a perpendicular fashion such that one opening of the vessel is submerged in liquid sample of interest. The liquid sample enters the vessel, either by capillary action or by applying negative pressure to the end of the vessel not submerged in liquid sample, drawing the sample up into the vessel. The vessel is then placed into the "plug-and-play" compression system, and connections are made as indicated in FIG. 19B. A liquid stream from an LC pump or positive pressure source, expels the target sample of interest from the vessel itself. The vessel having the compression fittings are designed to contain features allowing for robotic handling and manipulation. The vessels can either be re-usable or used as a one-time-use disposable item. For disposable vessels, only a single sample comes into contact with each vessel allowing for no sample-to-sample carryover or cross-contamination.

It is understood that both the gaseous or liquid sample vessel inserts may also contain columns, fits, filters, solid phase extraction, and reaction media.

Figure 20:
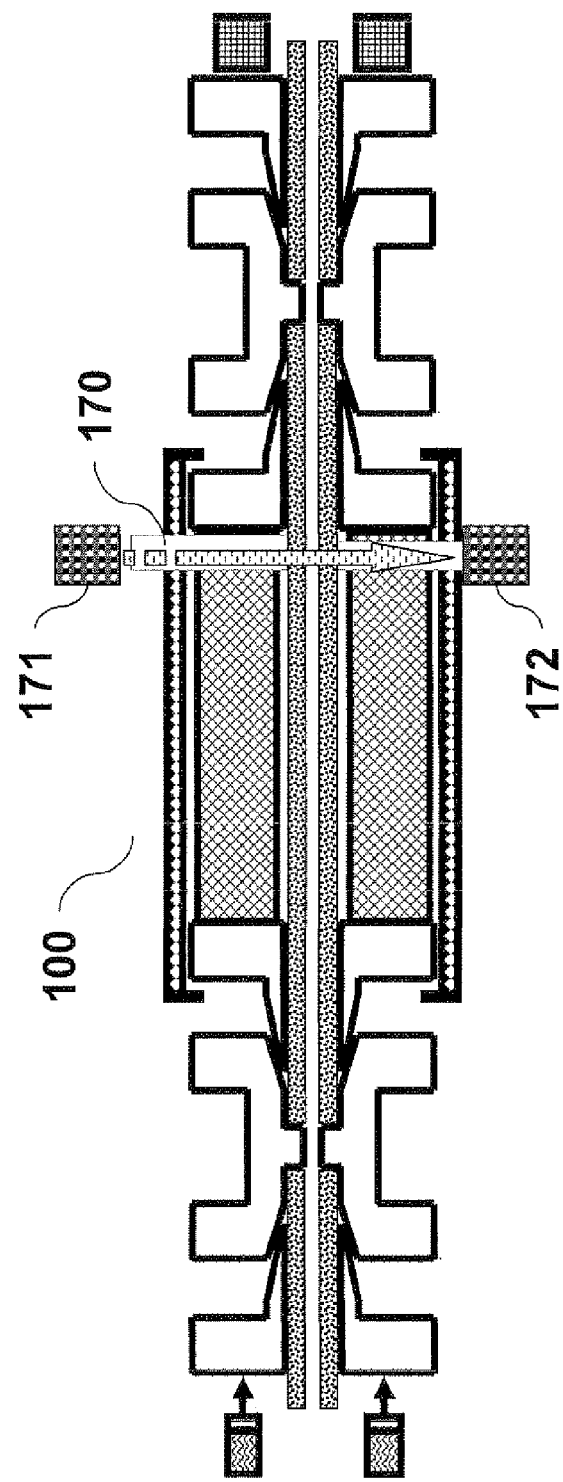
FIG. 20 is a cross-sectional view of the device containing an optical port, light source, and light-based detector.

Shown in FIG. 20 is an insert containing an integrated optical port channel 170. When the insert 100 is placed into the receiving hardware the light path generated from the light source 171, traverses the optical port channel 170 in the insert, and is in alignment with the optical detector 172. After alignment sample or analyte traveling through the tube or column can be detected by such techniques as visible, ultra-violet (UV), infrared, absorbance, transmission, or fluorescence. It is understood that the insert can contain a single or plurality of optical channels. In an alternative embodiment the optical channel through the insert is used to expose the sample or analyte to an energy source.

Figure 21:
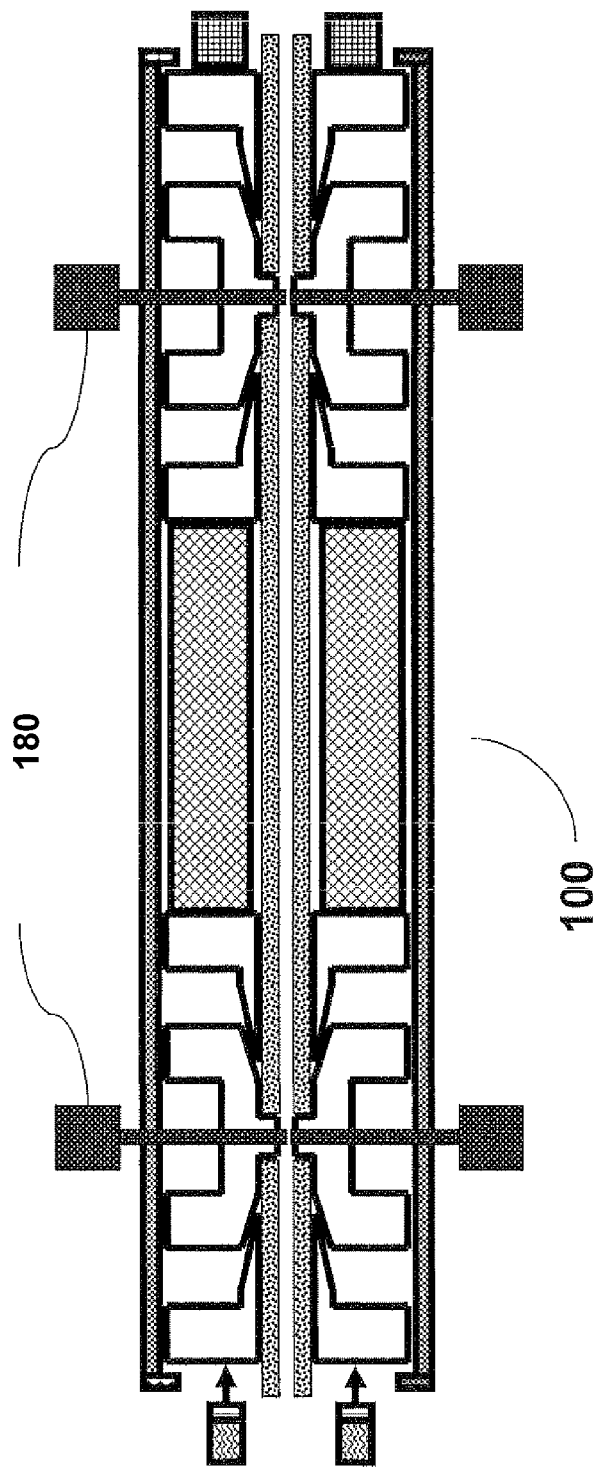
FIG. 21 is a cross-sectional view of the device containing ports for electrode structures.

Referring to FIG. 21, there is shown an insert 100 with electrodes 180 integrated into the insert 100. The insert 100 is placed into the receiving hardware and the electrodes 180 integrated in the insert 100 make contact with corresponding pads in the receiving hardware. The electrodes can perform electrochemical oxidation/reduction reactions, measure conductivity, pH, etc. Alternatively, the electrodes 180 can apply the electric potential needed to conduct capillary electrophoresis (CE), capillary electrochromatography (CEC), isoelectric focusing, or similar electric field applications. Additionally, the electrodes 180 can serve as a catalyst for on-line reactions.

Figure 22:
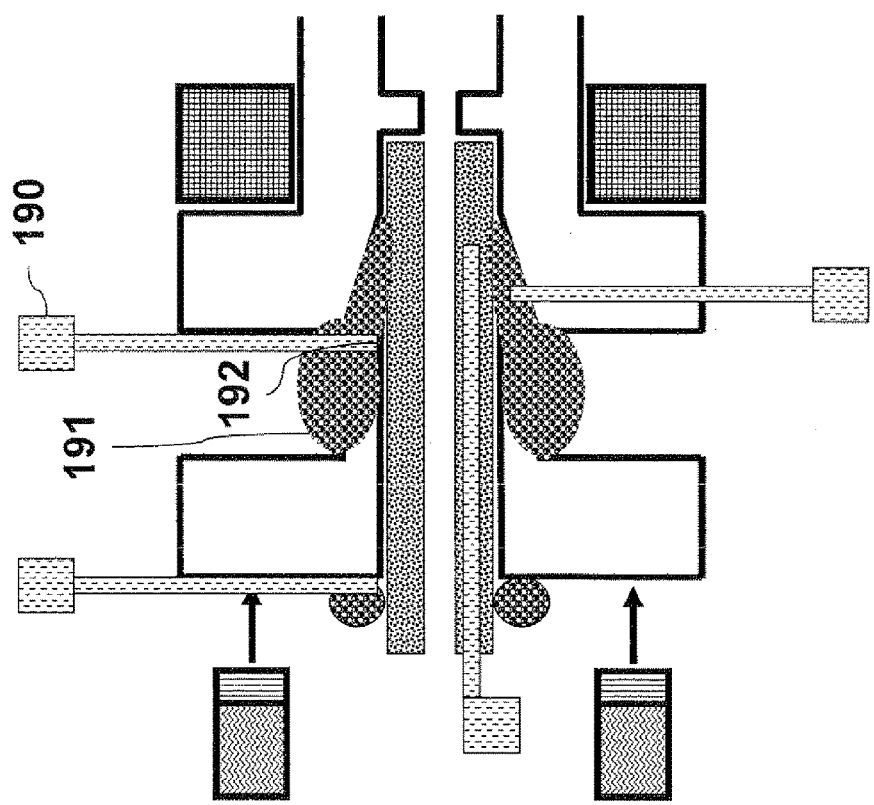
FIG. 22 is a cross-sectional view showing contact leak sensors with their distal ends located in close proximity to the seal and compression interface.

Referring to FIG. 22, there is shown a fitting assembly with leak sensors 190 located in close proximity to the seal and compression interface. The contact electrodes are in close proximity to the fluid seal junction where leaks are most likely to develop. In one embodiment the sensor is located within 500 µm of the leak resistant seal When a leak develops the fluid 191 comes into contact with the sensor material 192. The sensor may detect the leak by resistance, change in potential, reaction, voltage detection, current detection, circuit closure, etc. For leaks of small liquid volumes, as one would expect from techniques such as nanoLC, CE, CEC, etc., it is important the sensors are located in close proximity to the leak as evaporation prevents significant liquid build-up. A plurality of leak sensors can be positioned in many locations throughout a fitting assembly to isolate and diagnose component failure and system issues. The leak sensors are capable of detecting leaks of less than 1 mL/min. In one embodiment the leak sensors are capable of detecting leaks of less than 1000 nL/min. In an additional embodiment the leak sensors are capable of detection leaks of less than 20 nL/min. In one embodiment the leak sensor is disposed in the receiving port or ferrule. In an alternative embodiment the leak sensor is positioned between the receiving port and the ferrule.

In one embodiment of the present invention, an electrode is used to detect leaks. The electrode materials may include metals, metal mixtures or alloys, metal-semiconductor mixtures or alloys, conductive polymers, carbon, graphite, mixtures of carbon and polymers, plastics, or any combination thereof. The electrode can be of any shape. The electrode surface may be smooth or rough. The electrode surface are placed in the system where leak detection is desirable such as, but not limited to, integrated into the system via the connections themselves, in close proximity to the tubing, or through devices such as contact pads, clamps, sleeves, or wires. The sensor can be in the form of wire, contact pads, conductive materials or doped-materials. Examples include, but are not limited to, conductive collars, wires, contact pads, sleeves, or embedded electrodes placed in the desired zone for detection.

According to one aspect of this invention, the leak sensors is coated with alternative materials by dipping electrodes into a coating solution or deposited by gas phase deposition. In one embodiment the leak sensor is made of a conducting material that is deposited, evaporated, puttered, dip-coated, electroplated, electo-coated, or doped. The coating of an electrode is made by polymeric or other organic material growth in solution or in gas phase. In an alternative embodiment the leak sensor is glass, metal, plastic, polymer, alloy or doped material. In one embodiment the sensor is designed to be inert so to limit interactions or incompatibility with the sample or solution. The sensor surface area can be of various sizes and/or surface areas. In one embodiment the sensor is fully integrated within the device, including integration of processing and monitoring and control electronics. The sensor can either be a detector or send signals to a component or system. The processing, monitoring and control electronics are located off the device and the sensor only contains the detection component. Alternatively, the processing, monitoring and control electronics are integrated within the sensor. The sensor is connected to electronics via physical connections such as wires or conductive material connections or may communicate through wireless connections to remote electronics via radio frequency, infrared, blue tooth, RFID or other wireless formats.

Figure 23:
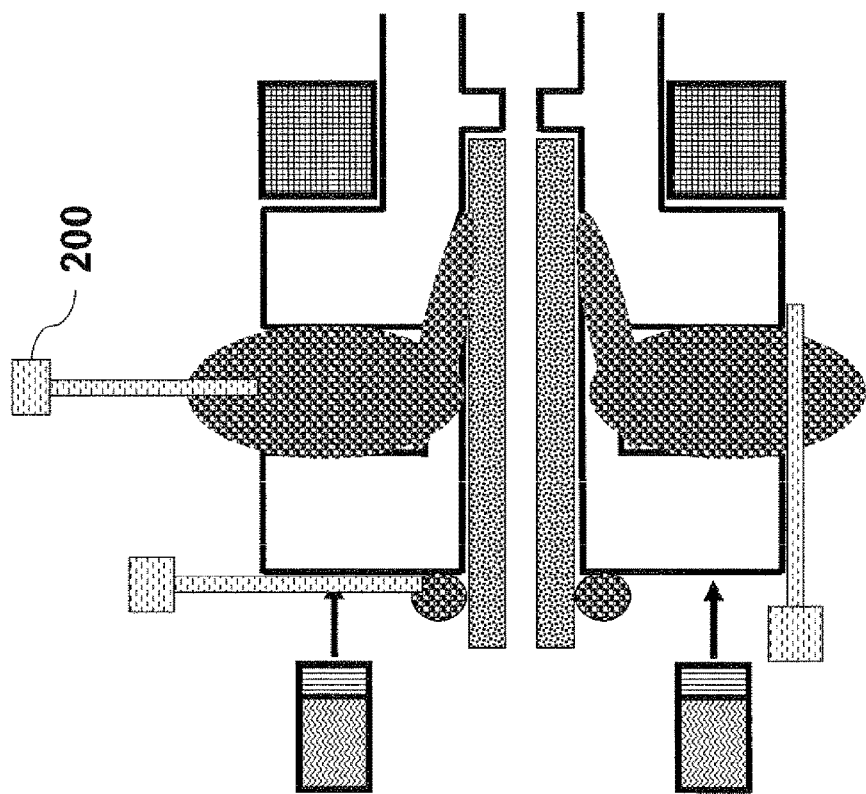
FIG. 23 is a cross-sectional view showing contact leak sensors located further in proximity from the seal and compression interface.

Shown in FIG. 23 is a "plug-and-play" compression fitting with contact leak sensors 200 positioned external to the outer fitting surfaces. As liquid leaks from the fitting, it fills the inner void of the fitting and the fluid will begin to protrude and touch the sensor. In one embodiment the fitting has a structure that helps to wick the fluid to the sensor or to a location in the insert where a sensor is strategically located. The connection can be coated with a hydrophilic surface or may use capillary action to deliver leaking liquid to the sensor. In one embodiment the sensor is located within 25,000 μm of the leak-resistant seal. In one embodiment the a narrow channel with a width of less than 500 μm is used to create the capillary action. In an alternative embodiment the narrow channel is less than 250 μm. A plurality of these sensors can be positioned in many locations throughout a fitting assembly to isolate and diagnose component failure and system issues. The leak sensors are capable of detecting leaks of less than 1 mL/min. In one embodiment the leak sensors are capable of detecting leaks of less than 1000 nL/min. In an additional embodiment the leak sensors are capable of detection leaks of less than 20 nL/min. Additionally, the leak sensor can be an electronic leak sensor capable of detecting conductivity, current, voltage, resistance, or change in electrical potential.

Figure 24:
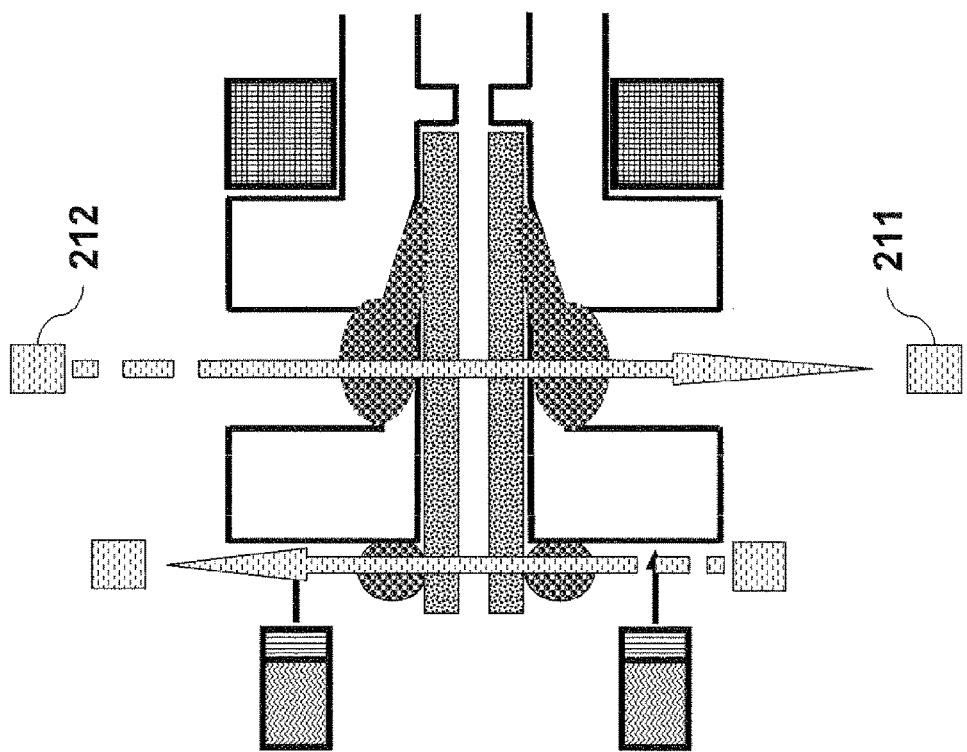
FIG. 24 is a cross-sectional view showing a non-contact, optical leak sensor using transmitted light through the leak prone regions internal to the fitting.

Shown in FIG. 24 is a "plug-and-play" fitting with non-contact optical-based leak sensors. The optical, light-based sensor uses light transmitted through an opening or passage within the fitting geometry. A light sensor 211 is aligned opposite the light source 212 in the light path so that it can measure the amount of transmitted light. Light sources include UV, visible, infrared, and laser-based. The optical sensor is capable of detecting light transmission, reflectance, absorbance, refractive indexes, and spectral changes. In an alternative embodiment the light sensors detect additional light measurements include refractive index, absorbance, and spectral changes. A plurality of sensors can be positioned in many locations throughout a fitting assembly to isolate and diagnose component failure and system issues. The leak sensors are capable of detecting leaks of less than 1 mL/min. In one embodiment the leak sensors are capable of detecting leaks of less than 1000 nL/min. In an additional embodiment the leak sensors are capable of detection leaks of less than 20 nL/min.

Figure 25:
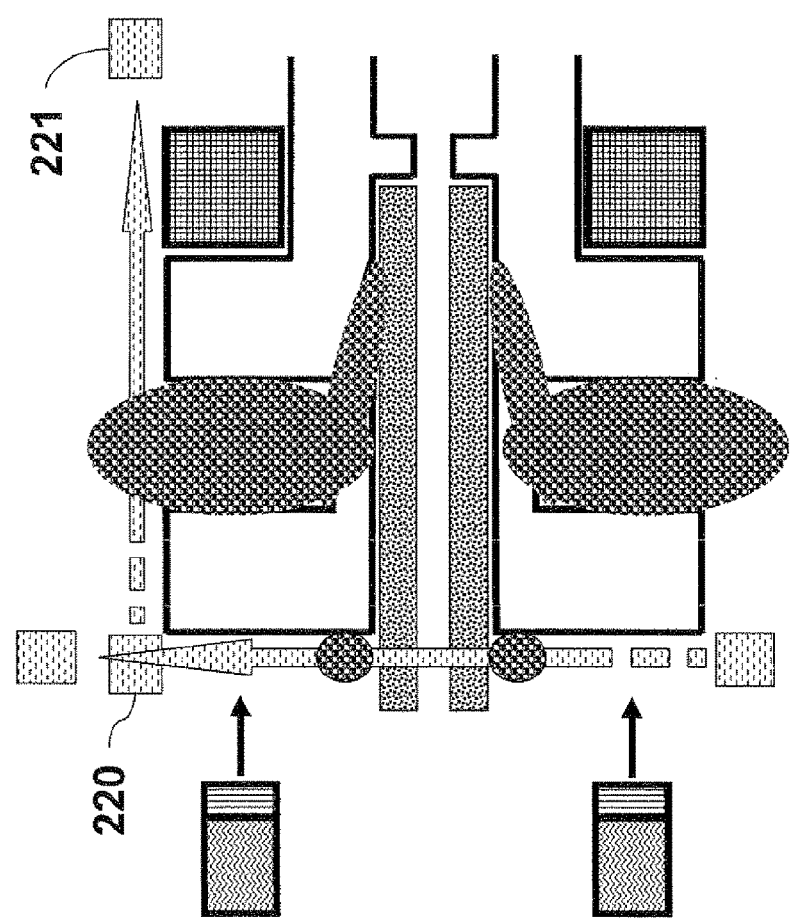
FIG. 25 is a cross-sectional view showing a non-contact, optical leak sensor using transmitted light, through the leak prone regions external to the fitting.

Referring to FIG. 25, there is shown a "plug-and-play" fitting with non-contact optical-based leak sensors. The optical, light-based sensor uses transmitted light to detect liquid that has leaked external to the fitting. An optical source 220 is positioned to send light adjacent to the outer surface of the fitting, and the sensor 221 is placed in alignment with the light path. As liquid leaks from the fitting, the change in transmitted light is measured. Light sources include UV, visible, infrared, and laser-based. In one embodiment the sensor is capable of measuring refractive index, absorbance, or spectral changes to detect leaks. A plurality of these sensors can be positioned in many locations throughout a fitting assembly to isolate and diagnose component failure and system issues. The leak sensors are capable of detecting leaks of less than 1 mL/min. In one embodiment the leak sensors are capable of detecting leaks of less than 1000 nL/min. In an additional embodiment the leak sensors are capable of detection leaks of less than 20 nL/min.

Figure 26:
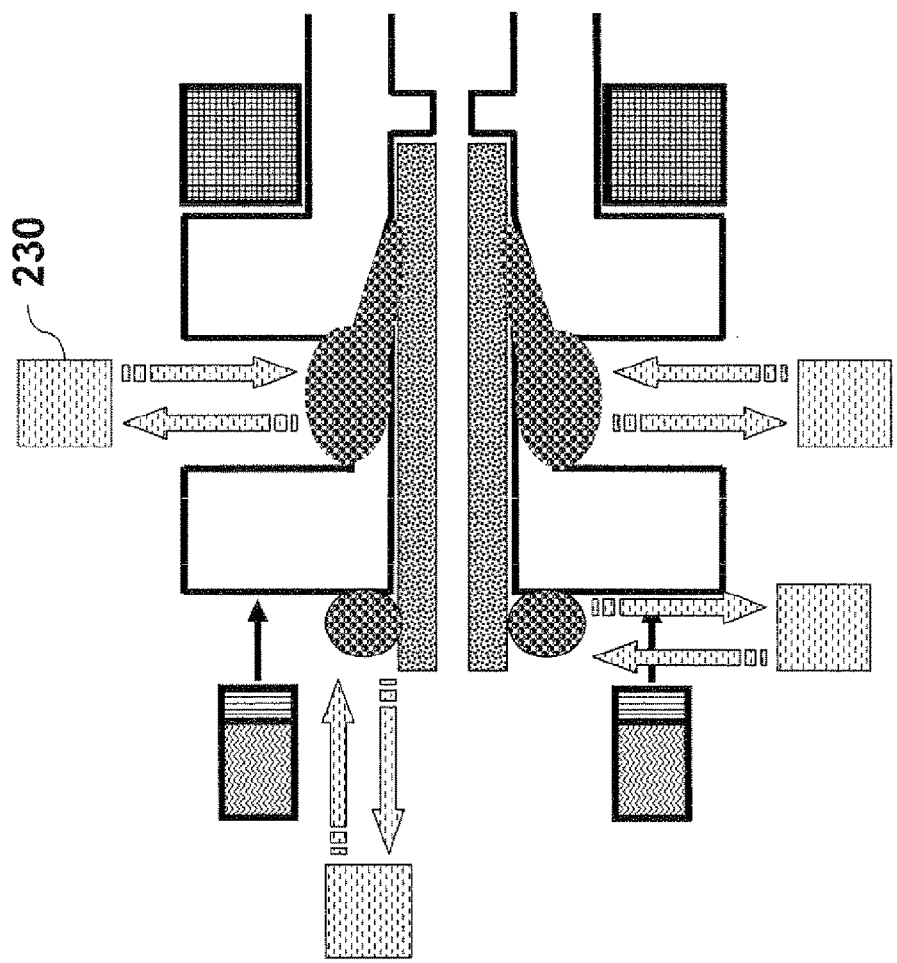
FIG. 26 is across-sectional view showing non-contact, reflected light, optical leak sensors where the light paths operate in close proximity to the fitting.

Shown in FIG. 26 is a "plug-and play" fitting with non-contact optical-based leak sensors utilizing reflected light from internal regions of the fitting. An optical source 230 is positioned to send light to open paths into the fitting, and reflected light is measured. If a leak develops, liquid in the light path will result in a change in the amount of reflected light read by the sensor 230. Light sources include UV, visible, infrared, and laser-based. A plurality of these sensors can be positioned in many locations throughout a fitting assembly to isolate and diagnose component failure and system issues. The leak sensors are capable of detecting leaks of less than 1 mL/min. In one embodiment the leak sensors are capable of detecting leaks of less than 1000 nL/min. In an additional embodiment the leak sensors are capable of detection leaks of less than 20 nL/min.

Figure 27:
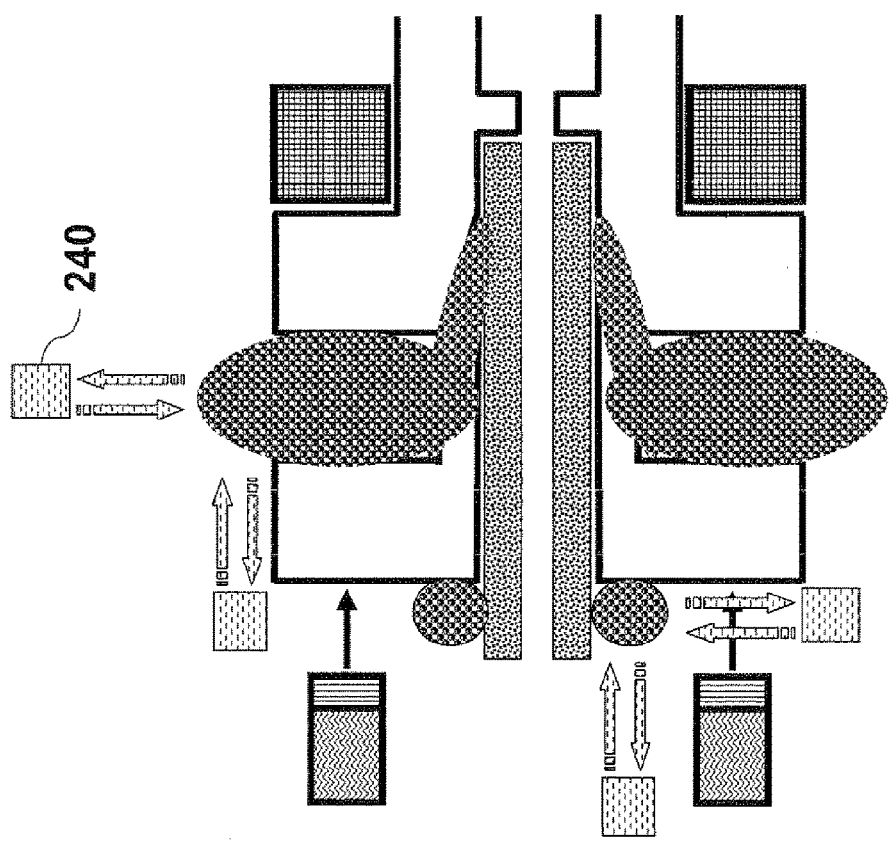
FIG. 27 is a cross-sectional view showing non-contact, reflected light, optical leak sensors where the light paths are further in proximity from the fitting.

Shown in FIG. 27 is a "plug-and-play" fitting with a non-contact optical-based sensor for detecting reflected light external to the fitting. An optical source 240 is positioned so that light reflecting external to the fitting can be measured. In the event that fluid leaks from the fitting and protrudes from or wets the external surfaces of the fitting, the sensor 240 detects a change in reflectance. Light sources include UV, visible, infrared, and laser-based. A plurality of these sensors can be positioned in many locations throughout a fitting assembly to isolate and diagnose component failure and system issues. The leak sensors are capable of detecting leaks of less than 1 m/min L. In one embodiment the leak sensors are capable of detecting leaks of less than 1000 nL/min. In an additional embodiment the leak sensors are capable of detection leaks of less than 20 nL/min.

Figure 28:
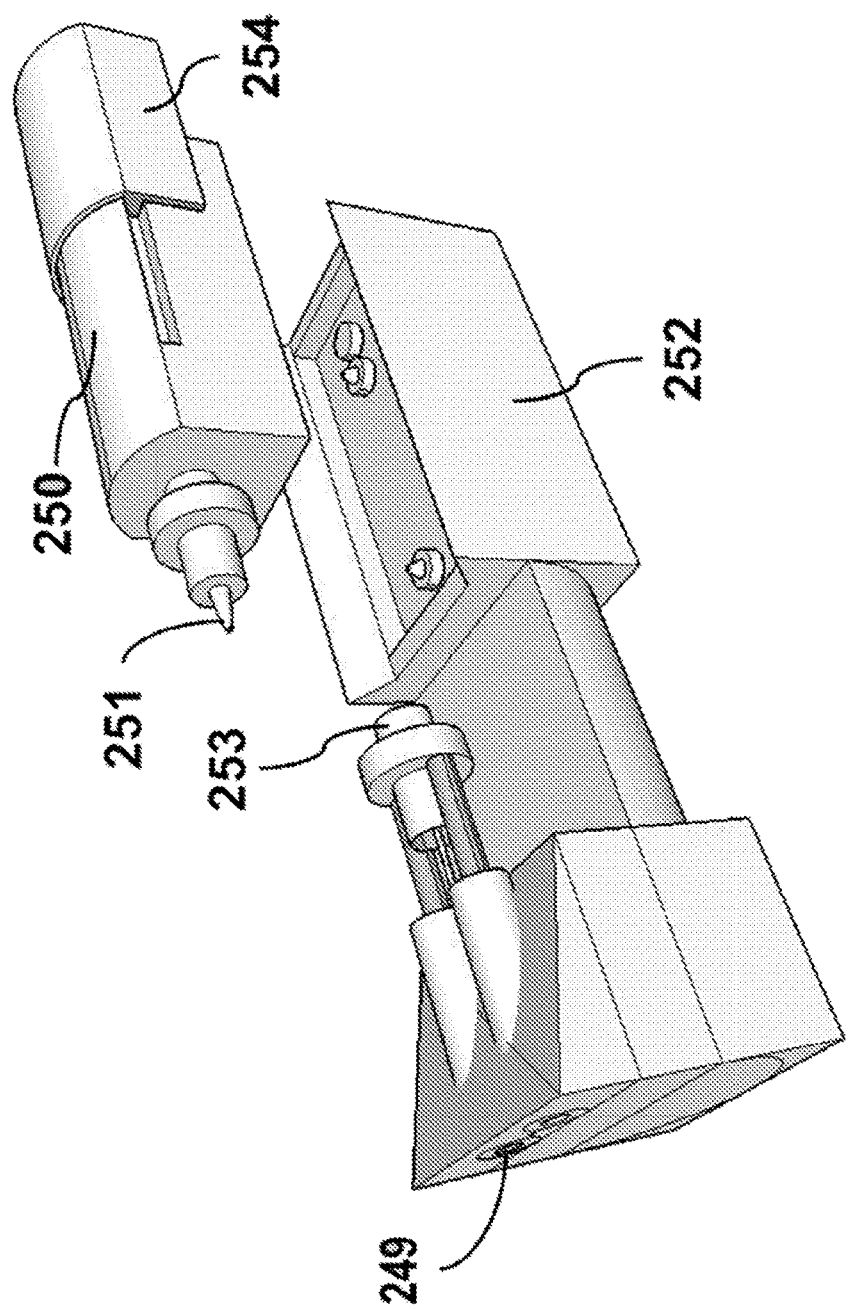
FIG. 28 is a drawing illustrating the docking hardware and the insert with a retractable sheath that protects exposed components.

Referring to FIG. 28, there is shown an embodiment of a "plug-and-play" nanoliquid chromatography and nanoelectrospray insert, and its receiving hardware showing inlet 249 for LC pump and autosampler. The insert 250 contains the "plug-and-play" ferrule 251, and the receiving hardware 252 contains the ferrule's corresponding receiving port 253. In one embodiment the insert 250 contains a nanoliquid chromatography capillary column, nanoelectrospray emitter, protective retractable sheath 254 to protect the spray emitter, and integrated diagnostic leak and nanoelectrospray sensors (whose electrical interconnects are not shown). The receiving hardware 252 ensures that the insert 250 is accurately positioned in front of the detector (not shown) to yield optimal results.

The insert 250 or the retractable sheath 254 can provide gas delivery for nebulization, auxiliary fluid, drying gases, curtain gas, or for change in gaseous atmosphere. In one embodiment the sheath 254 is made of a conductive or partially conductive material to provide other functionality where varying electrical potentials are applied for attributes such as electrical gate or field free region. The sheath can also act as the spray sensing device or electrode.

An insert 250 is placed into the receiving hardware 252 where one or more leak sensors are either integrated into or around the receiver port 253 or tube inlet ferrule 251. The sensors can be in the insert 250 and connected via electrical connection to the receiving hardware 252 or the sensors may be part of the receiving hardware 252 and in an appropriate position to detect liquid leaking. The sensors can be integrated, mechanically fixed, or casted into place. In an alternative embodiment, the insert contains sensors capable of measuring fluid flow rate, fluid pressure, fluid backpressure, electrical current, electrical voltage, electric field strength, electrospray current, gas velocity, gas pressure, fluid density temperature, absorbance, light transmission, reflectance, chemical detection, and optical detection.

In one embodiment, the insert 250 contains an electrospray emitter protected by a retractable sheath 254. Upon manual or automated placement of the insert 250, the connector is compressed via the compression fitting hardware the high pressure connection is made. The compression can be achieved by either manual intervention or via automation.

The receiving hardware 252 station can accept one or more inserts 250 and has manual or automated translational stages for aligning the insert 250 to a detector or to fluid processing instrumentation. Furthermore, the receiving hardware 252 can be adapted to use one or more inserts 250 in a serial or parallel fashion. In one embodiment the receiving hardware 252 has integrated electronics or interconnects for interfacing to the devices within the insert 250. The receiving hardware 252 allows for a means of interfacing the packaged device to detectors such as a mass spectrometer. The detector type may be of any type suitable for fluid processing.

The invention could also be used to perform on-line synthetic chemistry and to study on-line synthetic chemistry reaction kinetics. Reactants and analytes are injected into the fluid stream. Inserts containing integrated optical port channels, with a light source and detector monitor the reaction kinetics. Alternatively a detector external to the "plug-and-play" system, such as a mass spectrometer or UV detector receives the fluid stream and monitors the reaction kinetics. Alternatively, the insert contains an integrated, catalytic electrodes or light sources to perform reaction chemistry. With conventional flow-through reactor chemistry, the formation of reaction products that are not soluble and precipitate within the reactor is a major concern, due to clogging issues. The present invention allows for an in-line filter insert that can be replaced periodically in an automated fashion throughout the duration of the reaction and experiment. A time interval for component switching or alternatively, pressure and flow sensors is used to determine the appropriate time to change the filter or reaction chamber. The insert can contain an alignment device to ensure proper alignment in the docking hardware such as a physical protrusion, hollow channel, or optical sensing devices.

Figure 29A:
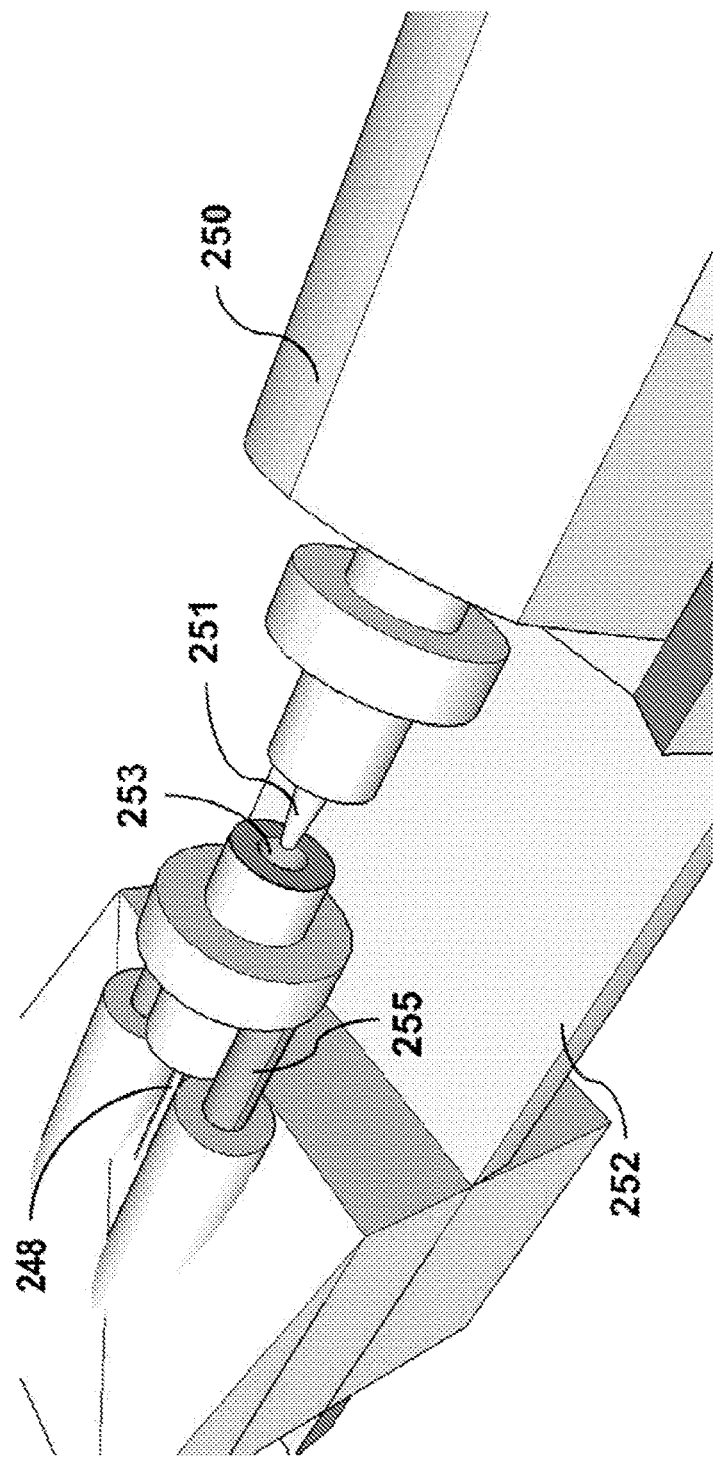
FIG. 29A shows the insert being placed into the docking hardware and the compression connection between these two components is about to be made.

Shown in FIG. 29A is an expanded view of the insert 250 in the receiving hardware 252 where the column inlet ferrule 251 and receiver port 253 are not sealed by the drive force compression mechanism 255.

Figure 29B:
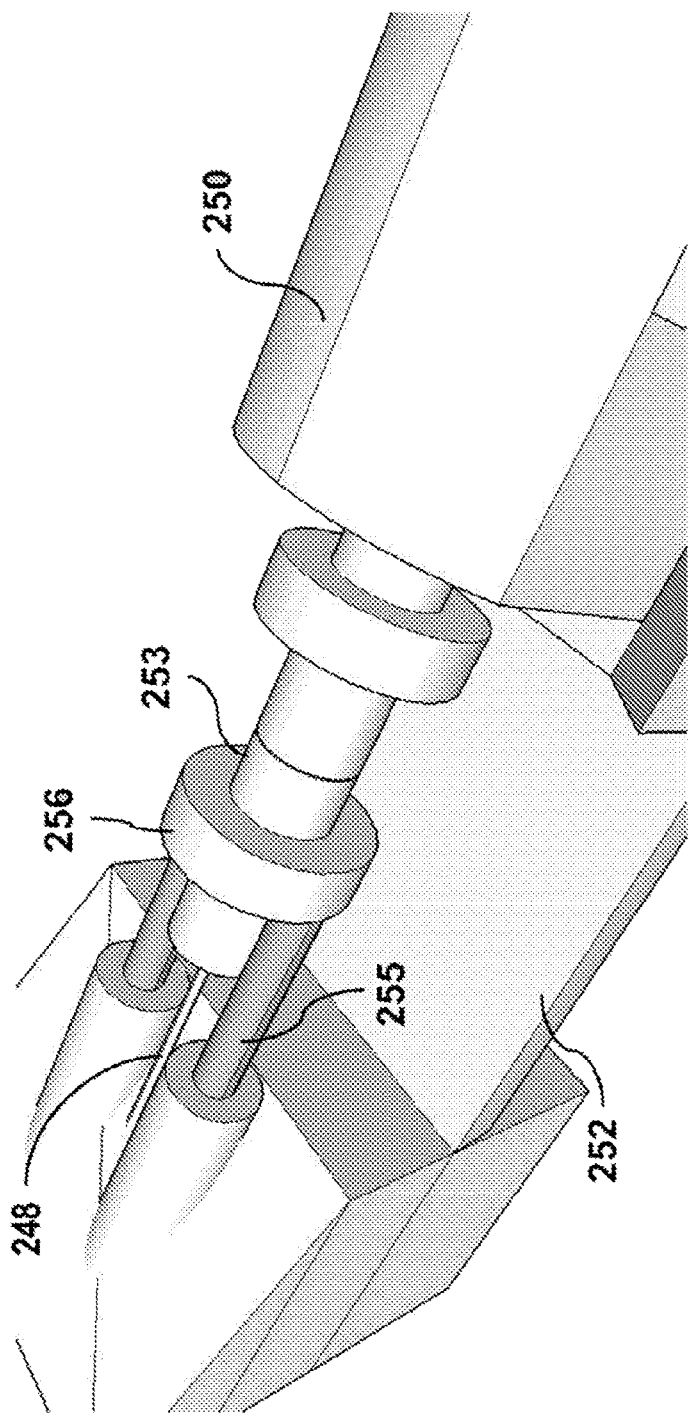
FIG. 29B shows the compression connection between the insert and the docking hardware.

Referring to FIG. 29B, there is shown the same expanded view as in FIG. 29A with the axial drive force applied by the compression mechanism 255 to the receiving port 253, sealing the column. The receiving port is affixed to the drive force mechanism which is built into the receiving hardware. Upon manual or automated placement of the insert 250 into the receiver hardware 252, the high pressure connection is made. This axial drive force results in the receiving port engaging and compressing the ferrule onto the capillary nanoliquid chromatography column inlet connecting the tubing 248 to the LC pump and autosampler. This seal has none of the negative attributes of conventional torque fittings that rotate and twist ferrules and capillary columns. The force measurement sensor 256 provides monitoring and control for accurate, precise, and reproducible sealing forces. The drive force can be a lead screw, motor servo motor, pressure system, pneumatic device, hydraulic device, magnet or spring. In an alternative embodiment, the drive force compression mechanism can compress a plurality of compression fittings in series or parallel. In an alternative embodiment, a plurality of drive force mechanisms are used to compress a plurality of compression fittings in series or parallel.

Figure 29C:
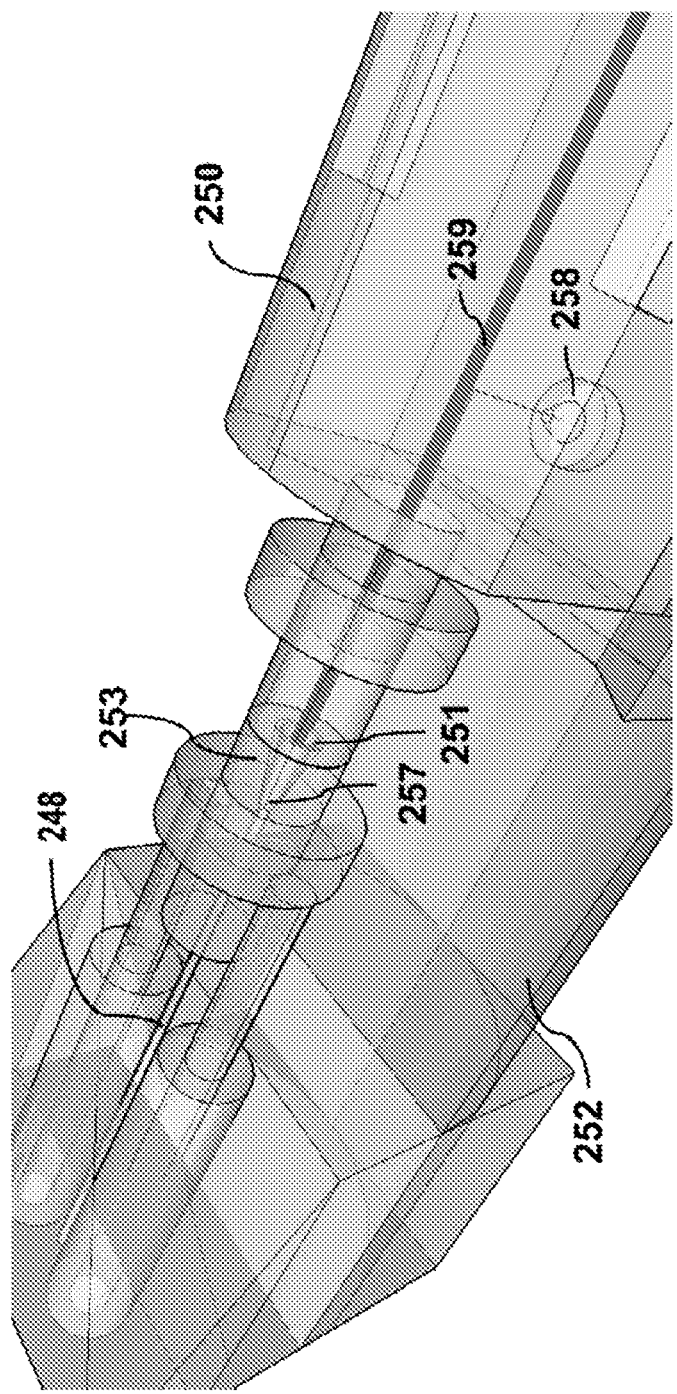
FIG. 29C is an x-ray view of the compression connection between the insert and the docking hardware.

Shown in FIG. 29C is the x-ray view of FIG. 29B showing the insert in the receiving hardware with the compression seal made between the ferrule 251 from the insert 250 and the receiving port 253 from the receiving hardware. The leak sensor electrode 257, at the compression connection with its interconnect contact pad 258 at the base of the insert is shown. The nanoliquid chromatography column 259, which is imbedded in the insert 250, is also shown. It is understood that although the invention has been shown as compressing the ferrule on the tube an alternative embodiment includes the use of a sleeve placed over the tube such that the ferrule is compressed by the receiver port, the ferrule compresses on the sleeve and subsequently, the sleeve compresses on the tube. Sleeves can act as an interface allowing the use of ferrules of a single size to seal various sized tubing.

Figure 30A:
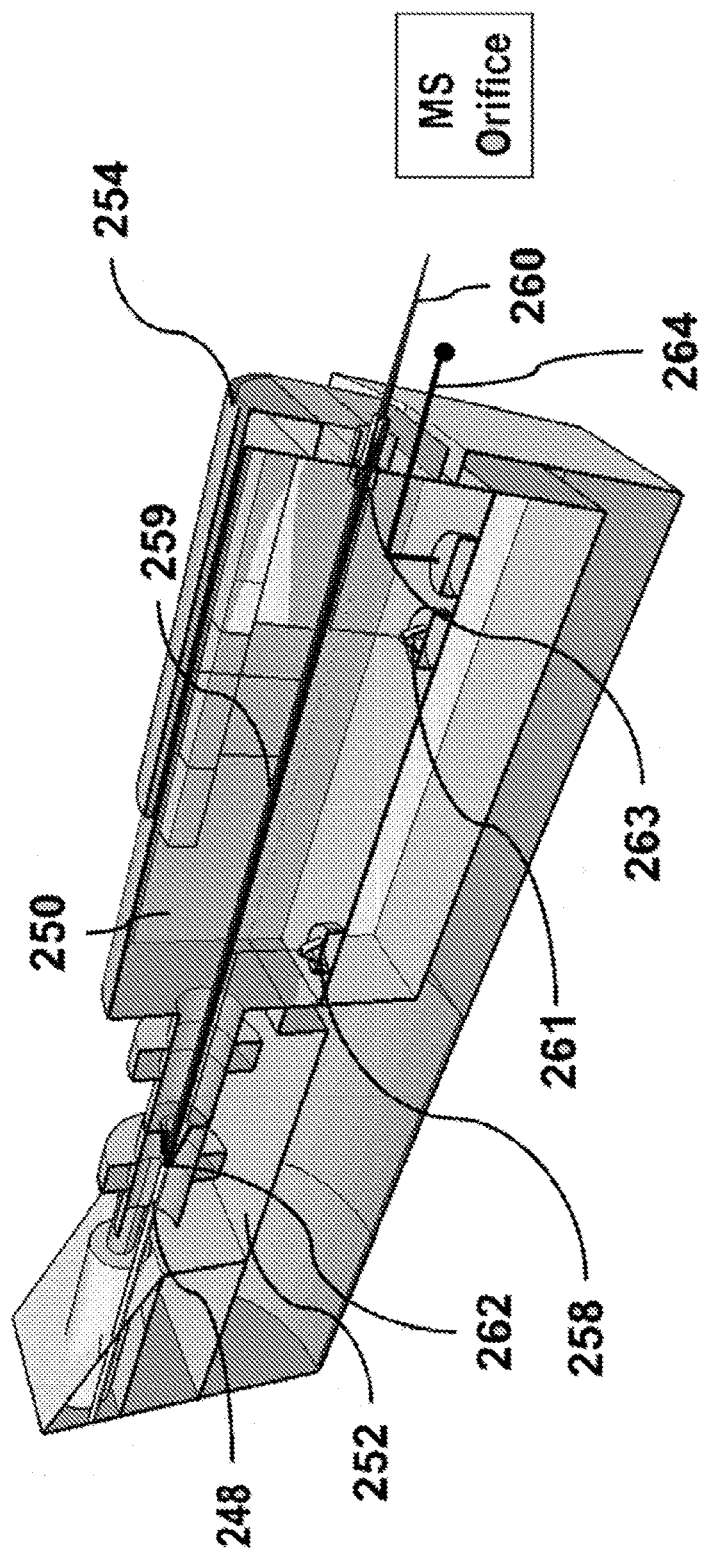
FIG. 30A is a cross-sectional view with the insert placed in the docking hardware and the sheath retracted exposing the spray emitter.

Referring to FIG. 30A, there is shown a cross-sectional view with the insert 250 placed in the receiving hardware 252 and the sheath 254 retracted exposing the spray emitter 260. The nanoLC column 259, spray emitter 260 and diagnostic sensors, all of which are imbedded in the insert, are shown. At this point the system is ready to perform sample analyses. As shown in this embodiment two diagnostic leak sensors are integrated into the insert, one for detecting leaks at the column inlet seal 262, and a second 261 for monitoring leaks at the column-to-emitter interface connection 263.

Also shown is the electrospray diagnostic sensor 264 which monitors the spray current when in operation.

Figure 30B:
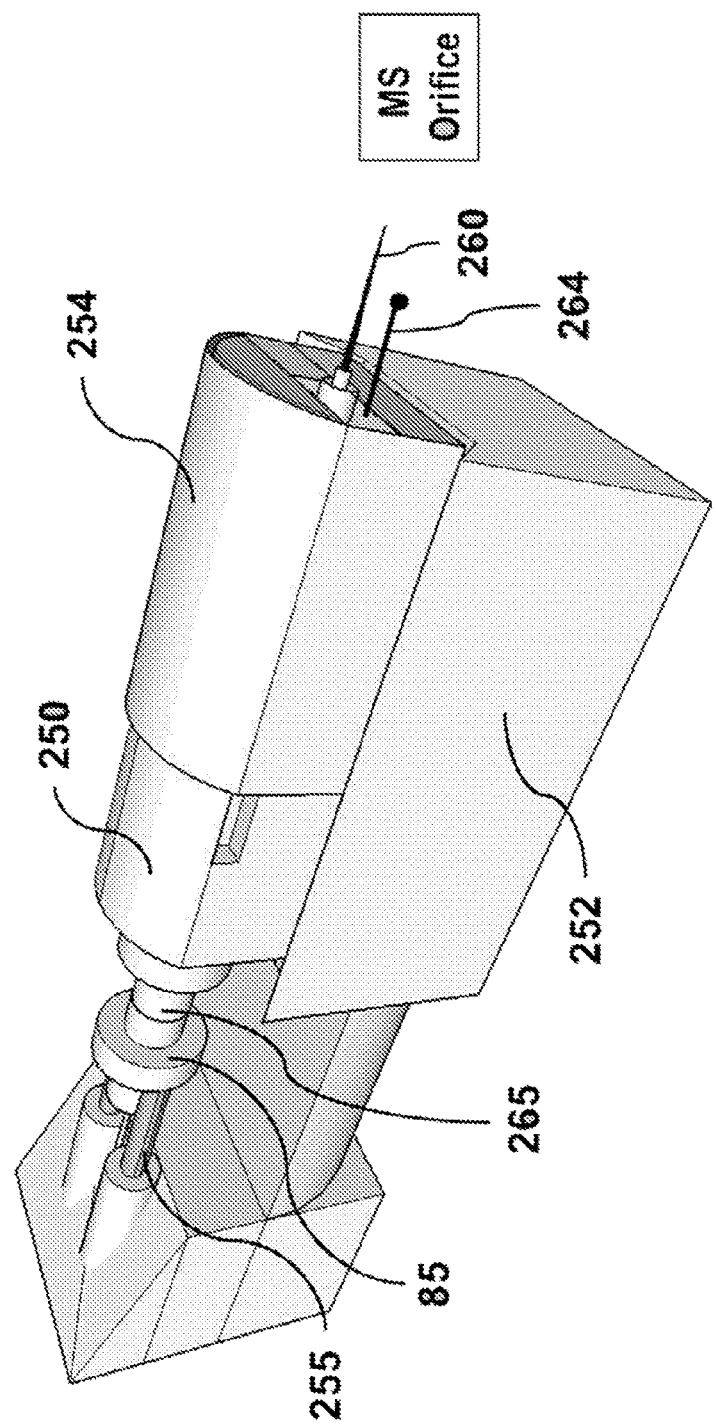
FIG. 30B shows the insert placed in the docking hardware, the compression connection made, and the sheath retracted exposing the spray emitter.

Shown in FIG. 30B is the insert 250 placed in the receiving hardware 252, the compression connection 265 made, and the sheath 254 retracted exposing the spray emitter 260. The receiving hardware would be connected to electronics and a data system for sensor monitoring and system control.

Figure 31:
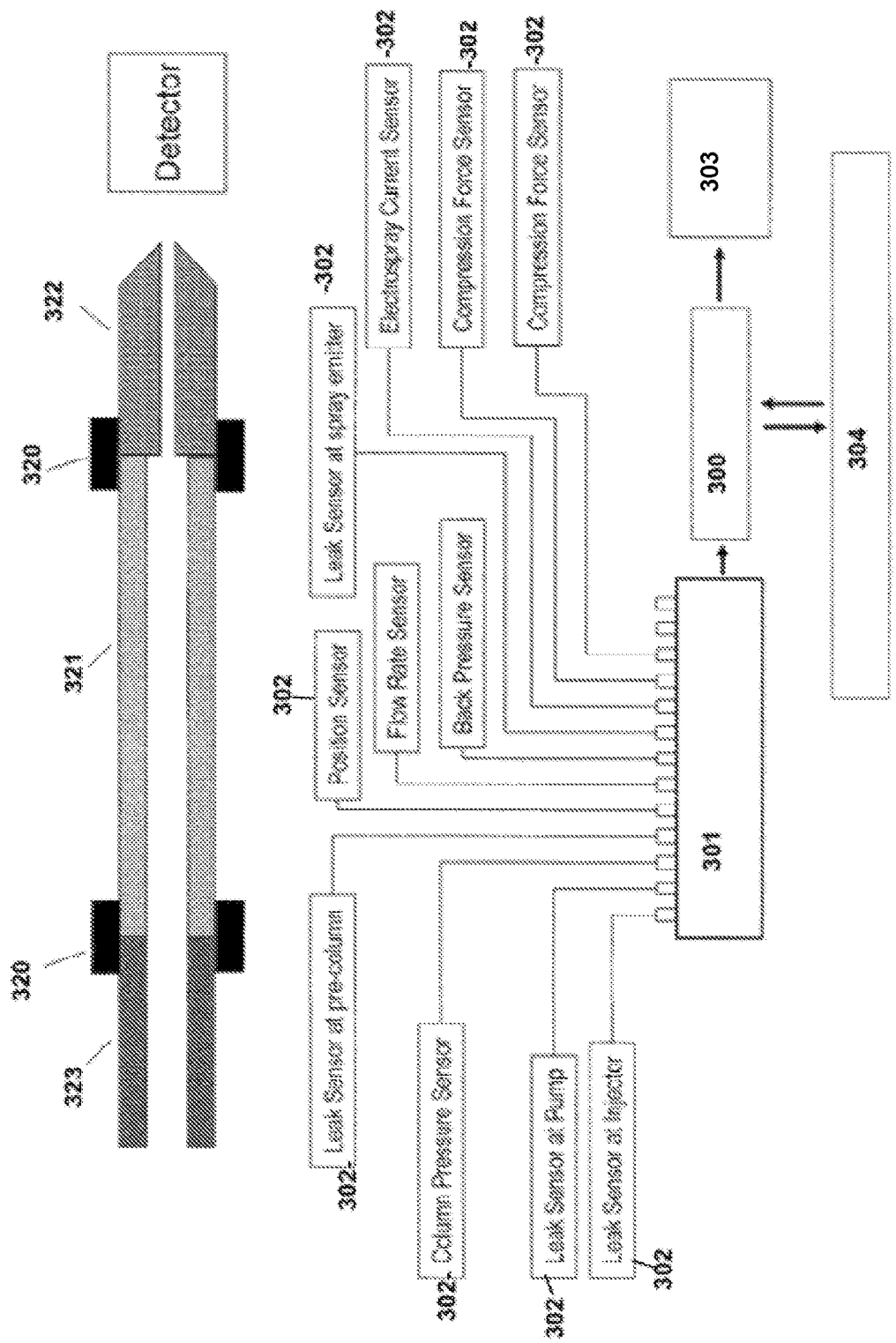
FIG. 31 illustrates system integration. The data system would collect feedback from the sensors, perform robotic manipulation, and manage communication input and output.

Referring to FIG. 31, there is illustrated system integration. The data system 300 collects feedback 301 from the sensors 302, performs robotic manipulation 303, and manages communication input and output 304. External communication input and output could be wire or wireless via internet, phone, RF, or Bluetooth.

In one embodiment the liquid chromatography electrospray system has one or more sensors that include liquid detection, liquid flow rate, fluid pressure, fluid backpressure, electrical current, electrical voltage, electric field strength, electrospray current, gas velocity, gas pressure, fluid density temperature, absorbance, light transmission, chemical detection, and optical detection.

The placement of the sensors may be invasive or non-invasive in nature. The sensors may be part of the chromatography wall surface via embedding, or as part of the actual structure, or as part of the fitting components. Alternatively the sensors may be located in varying proximity to the desired monitoring region, in either the insert or receiving hardware. According to one embodiment of this invention, the electrospray sensors may detect spray current, electric field strength, droplet size. The electrospray sensors may stand alone, be integrated with the consumable components, the insert, or be part of a mass spectrometer system.

The system has ability to self-diagnose certain system malfunctions including, but not limited to liquid or gas leaks, and changes in electrical potentials, backpressure, column pressure, optical spectrum, electrochemistry, electrospray current, chromatographic performance, and those alike.

When the sensors indicate the system is malfunctioning, the data monitoring and control system triggers the robotics to change out the component with an appropriate replacement part. Additionally, the data monitoring and control system has the ability to send electronic information such as email or a message on a communications pager or phone system to a pre-determined user.

In one embodiment, upon instruction from a control unit, the insert may be replaced or substituted in an automated fashion via robotics. The "plug and play" or quick connect fittings are released by the compression system 320 allowing robotics to remove and replace the insert. The insert 321 may be of the same type or a different variety. This allows for a replacement of a malfunctioning components or for substitution of a different type of separation for varying applications. (Such as pre-column 323 or columns with different stationary phases, or the like.) The emitter 322 may be replaced along with the column or remain in the system and similarly reconnected to the replacement column.

In one embodiment, upon instruction from a control unit, the spray emitter may be replaced or substituted in an automated fashion via robotics. The "plug and play" or quick connect fittings are released by the compression system allowing robotics to remove and replace the spray emitter. The spray emitter column may be of the same type or a different variety. This allows for a replacement of a malfunction of worn-out part(s) or for substitution of a different type of emitter for varying applications. The column may be replaced along with the emitter or remain in the system and similarly reconnected to the spray emitter.

The type of column is not limited to any one type and can include affinity, reversed-phase, normal phase, carbon phase, monolithic-based, ion exchange, antibody, trap, guard, solid phase, molecular weight, and those alike. Furthermore, this functionality could be either serial or orthogonal in nature, with a single column or plurality of columns.

The replacement mechanism may be made by such techniques as a robotic arm with pick-a-place, cassette-to-cassette, cartridge-based, pre-loaded magazine, or those alike. The inserts would be casted, pre-casted, molded, machined, or compiled substrate devices.

FIG. 32 shows a diagram where a column and/or emitter "plug and play" device array 320 containing a plurality of inserts operating or robotically manipulated as a linear 321 or radial array 322. The use of the inserts could be serial or parallel in nature. Parallel inserts allows different inserts to be quickly interchanged, or a second insert may be used while the first insert undergoes a conditioning treatment such as a wash or bake. In another embodiment, there may be multiple inserts within cartridges that are manually or robotically replaced. The casting may have other features such as ports for makeup fluids or gases. In one embodiment the final packaged device can have ports and architecture for entry and directional delivery of a nebulizing gas to the spray region.

The inserts of the system can have automated replacement or substitution of parts. The replacement or substitution may be conducted via a pick-and-place approach or via an array such as a linear or radial array. The device may used in parallel for conducting a simultaneous analysis, used in sequence, or in a staggered fashion.

In one embodiment, the column, connection fittings, sensors and majority of the spray emitter (the emitter end must be exposed for proper operation) are encased in a single package. This is accomplished with a preformed structure of multiple inserts or by casting the column, sprayer, sensors, and fittings as one integrated insert such that they are protected from damage or tampering during use or handling. The fittings and sensors can be fixed in place such that they are maintained in an accurate and precise position. The end of the spray emitter may be temporarily covered by a retractable sheath structure to protect the device until installation and operation of the system. The insert is made of thermally conductive materials when temperature control is desired. The insert may be made into any shape that allows for integration with the accepting hardware, such as being keyed for precise and accurate placement, and for aligning of the sensor interconnections. In one embodiment the insert may have features allowing a gas or liquid to enter into the device for thermal control, or may be thermally conductive to conduct heat or cold to the inner parts such as the column. Additionally, the insert contains other partial detectors components such as optical windows for ultraviolet detection or exposure to the chemical stream for chemical detectors such as oxidation, reduction, or electrochemical reactions. In one embodiment the insert incorporates alignment features for positioning into the receiving hardware, windows for optical, absorbance, refractive index, or fluorescence detection and access ports for additional fluidic manipulation such as splitting flow or providing make-up flow.

Example

A nanoLC column is constructed and coupled to a nano-electrospray emitter (the emitter can be the same substrate or a separate substrate and coupled). A "plug and play" fitting is placed on the column's inlet and a second fitting is placed on the column's exit if the column and emitter are to be separate substrates. Conductive sensors with leads are place at the column inlet and between the column's exit and nanoelectrospray emitter connection. All critical alignments are made and the device is casted in a curable or hardening agent (such as a polymer) except for the column inlet and a partial zone at the spray emitter's end. The casting/mold creates an insert in a shape that fits into an accepting device in an accurate and precise orientation. A protective, retractable sheath is incorporated and positioned over the spray emitter end, eliminating the potential for damage by human intervention. The device is now protected and components are fixed in place. The compiled liquid chromatography electrospray device can be placed manually or automatically via robotics into the receiving hardware, and the column inlet connection is made manually or robotically via a compression mechanism device. The receiving hardware also has corresponding electrical contacts to the sensors and upon placement of the device in the hardware contacts are made. An electrospray current sensor is located in close proximity to the electrospray region. Column pressure and flow sensors are located pre-column. Upon system start up, a control data system monitors the sensors and records baseline values. Control electronics and a data system monitor the sensors during system operation. In combination the sensors now monitor system operation. For example if the spray sensing signal decreases and a leak is detected at the column exit/emitter interface, the emitter is malfunctioning, or if the spray current sensor signal is low and a leak is detected at the column inlet, the column or column connection is malfunctioning. Additional sensors diagnose other parts of the hardware such as the pumps and the injector system. If no leaks are detected at either the column or the sprayer, ion current is low, and the pump pressure decreases, the autosampler maybe malfunctioning. The user can configure the sensors and the information the sensors provide as appropriate, to monitor system performance.

Although the preferred embodiment of the present invention is shown, it will be understood that those skilled in the art that other embodiments can be used without departing from the scope of the invention. For example, in the fitting assemblies shown in the figures, the ferrules and receiving ports can be interchanged.

The invention has been described with reference to a preferred embodiment. However, it will be appreciated that variations and modifications can be effected by a person of ordinary skill in the art without departing from the scope of the invention.

What is claimed is:

1. A system for the automated compression connection of fluidic components comprising:
   receiving hardware comprising a conduit having an exit opening with a first mating surface of a compression connection and configured to align an insert placed therein;
   an interchangeable plug-and-play consumable insert configured for automated connection and comprising a conduit having an entry opening with a second mating surface of the compression connection;
   a drive force mechanism; and
   at least one mechanical support, wherein the drive force mechanism and the at least one mechanical support are each located in the receiving hardware, wherein the insert placed therein is disposed between the at least one mechanical support and the drive force mechanism, and wherein the drive force mechanism is configured to apply a substantially axial drive force opposed by the at least one mechanical support to align and compress the first and second mating surfaces together and create a leak-resistant seal at the compression connection between the insert and the receiving hardware, such that the system provides automated alignment and sealing of the insert.

2. The system of claim 1, wherein the interchangeable plug-and-play consumable insert comprises an electrospray emitter.

3. The system of claim 1, wherein the interchangeable plug-and-play consumable insert comprises a chromatography column and electrospray emitter.

\* \* \* \* \*